United States Patent
Mizuno et al.

(10) Patent No.: US 11,905,240 B2
(45) Date of Patent: Feb. 20, 2024

(54) CYCLOPROPYL ETHYLENE COMPOUND AND ARTHROPOD PEST CONTROL COMPOSITION CONTAINING SAME

(71) Applicant: SUMITOMO CHEMICAL COMPANY, LIMITED, Chuo-ku (JP)

(72) Inventors: Hajime Mizuno, Takarazuka (JP); Motohiro Nakajima, Takarazuka (JP); Kazuya Ujihara, Edogawa-ku (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 704 days.

(21) Appl. No.: 17/041,205

(22) PCT Filed: Mar. 27, 2019

(86) PCT No.: PCT/JP2019/013055
§ 371 (c)(1),
(2) Date: Sep. 24, 2020

(87) PCT Pub. No.: WO2019/189286
PCT Pub. Date: Oct. 3, 2019

(65) Prior Publication Data
US 2021/0032190 A1    Feb. 4, 2021

(30) Foreign Application Priority Data
Mar. 28, 2018 (JP) .................. 2018-061364

(51) Int. Cl.
| C07C 69/734 | (2006.01) |
| A01N 37/36 | (2006.01) |
| A01N 43/40 | (2006.01) |
| C07D 213/55 | (2006.01) |

(52) U.S. Cl.
CPC ............ *C07C 69/734* (2013.01); *A01N 37/36* (2013.01); *A01N 43/40* (2013.01); *C07D 213/55* (2013.01)

(58) Field of Classification Search
CPC .................................................. C07C 69/734
See application file for complete search history.

(56) References Cited

U.S. PATENT DOCUMENTS

| 5,026,874 A | 6/1991 | Larkin et al. |
| 5,294,628 A | 3/1994 | Schuetz et al. |
| 5,356,931 A | 10/1994 | Kirstgen et al. |
| 11,490,619 B2 * | 11/2022 | Semba .................. C07C 69/734 |

FOREIGN PATENT DOCUMENTS

| CN | 201522331 A | 6/2015 |
| CN | 107207438 A | 9/2017 |
| CN | 107708420 A | 2/2018 |
| JP | 2-180866 A | 7/1990 |
| JP | 4-279504 A | 10/1992 |
| WO | WO 95/30639 A1 | 11/1995 |

OTHER PUBLICATIONS

International Search Report dated May 21, 2019 in PCT/JP2019/013055, 2 pages.
International Preliminary Report on Patentability and Written Opinion dated Sep. 29, 2020 in PCT/JP2019/013055 (submitting English translation only), 5 pages.
"The Pesticide Manual"—17th edition, BCPC Publications, ISBN 978-1-901 396-88-1, 2015, pp. 1351-1357 with cover pages.
Extended European Search Report dated Feb. 16, 2022 in European Patent Application No. 19778016.6, 6 pages.
Combined Chinese Office Action and Search Report dated Oct. 8, 2022 in Chinese Patent Appiication No. 201980021883.5 (with Engiish translation), 15 pages.
Indian Office Action dated Apr. 5, 2022 in Indian Patent Application No. 202047043573, 5 pages.

* cited by examiner

*Primary Examiner* — Golam M Shameem
(74) *Attorney, Agent, or Firm* — Oblon, McClelland, Maier & Neustadt, L.L.P.

(57) ABSTRACT

The present invention provides a compound that have excellent harmful arthropod controlling effects, the compounds being represented by formula (I) [wherein $R^1$ represents a hydrogen atom etc., and $R^{21}$, $R^{22}$, $R^{31}$ and $R^{32}$ are identical to or different from each other and each represents a hydrogen atom etc., $Q^1$, $Q^2$, $Q^3$, $Q^4$ are identical to or different from each other and each represents CH etc.], as well as a composition comprising the same, and a method for controlling harmful arthropod comprising applying the same.

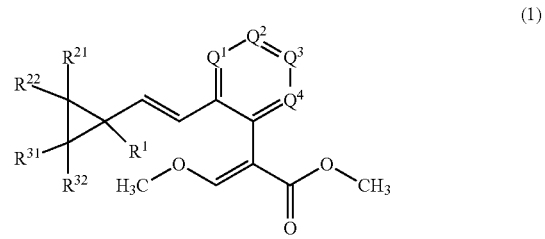

(1)

8 Claims, No Drawings

CYCLOPROPYL ETHYLENE COMPOUND AND ARTHROPOD PEST CONTROL COMPOSITION CONTAINING SAME

TECHNICAL FIELD

This application claims priority to and the benefit of Japanese Patent Application Nos. 2018-061364 filed Mar. 28, 2018, the entire contents of which are incorporated herein by reference.

The present invention is related to a certain class of cyclopropyl ethylene compound and a composition for controlling harmful arthropod comprising the same.

BACKGROUND ART

To date, in order to control harmful arthropods, some compounds have been studied and come into practical use (see Non-Patent Document 1).

CITATION LIST

Non-Patent Document

Non-Patent Document 1: The Pesticide Manual—17th edition, BCPC Publications, ISBN 978-1-901396-88-1

SUMMARY OF THE INVENTION

Problems to be Solved by Invention

An object of the present invention is to provide a compound having an excellent efficacy for controlling harmful arthropods.

Means to Solve Problems

The present invention includes the followings.
[1] A compound represented by formula (I):

[wherein
R$^1$ represents a C1-C3 alkyl group which may optionally have one or more halogen atoms or a hydrogen atom,
R$^{21}$, R$^{22}$, R$^{31}$ and R$^{32}$ are identical to or different from each other and each represents a C1-C4 chain hydrocarbon group which may optionally have one or more halogen atoms, a halogen atom, or a hydrogen atom,
Q$^1$ represents CX$^1$ or a nitrogen atom,
Q$^2$ represents CX$^2$ or a nitrogen atom,
Q$^3$ represents CX$^3$ or a nitrogen atom,
Q$^4$ represents CX$^4$ or a nitrogen atom, and
X$^1$, X$^2$, X$^3$ and X$^4$ are identical to or different from each other and each represents a C1-C4 chain hydrocarbon group {the C1-C4 chain hydrocarbon group may optionally have one or more substituents selected from the group consisting of a C1-C3 alkoxy group and a halogen atom}, a C1-C4 alkoxy group which may optionally have one or more halogen atoms, a halogen atom, or a hydrogen atom.](hereinafter, referred to as "Present compound" or "Compound of the present invention").

[2] The compound according to [1] wherein Q$^1$, Q$^3$ and Q$^4$ are CH, and Q$^2$ represents CX$^2$.
[3] The compound according to [1] or [2] wherein Q$^2$ represents CCH$_3$.
[4] The compound according to [1] or [2] wherein Q$^2$ represents CH.
[5] The compound according to any one of [1] to [4] wherein R$^1$ represents a hydrogen atom.
[6] The compound according to any one of [1] to [5] wherein R$^{21}$, R$^{22}$, R$^{31}$ and R$^{32}$ represent a hydrogen atom.
[7] A composition for controlling harmful arthropod comprising the compound according to any one of [1] to [6] and an inert carrier.
[8] A method for controlling harmful arthropod which comprises applying an effective amount of the compound according to any one of [1] to [6] to a harmful arthropod or a habitat of the harmful arthropod.

Effect of Invention

The present invention can control harmful arthropods.

MODE FOR CARRYING OUT THE INVENTION

The substituent(s) as described herein is/are explained.
The term "halogen atom" represents fluorine atom, chlorine atom, bromine atom, or iodine atom.
When the substituents have two or more halogen atoms, these halogen atoms may be identical to or different from each other.
The expression of "CX-CY" as used herein represents that the number of carbon atom is from X to Y. For example, the expression of "C1-C4" represents that the number of carbon atom is from 1 to 4.
The term of "chain hydrocarbon group" represents an alkyl group, an alkenyl group, or an alkynyl group.
Example of the term of "alkyl group" include methyl group, ethyl group, propyl group, isopropyl group, 1-methylpropyl group, butyl group, and tert-butyl group.
Example of the term of "alkenyl group" include vinyl group, 1-propenyl group, 2-propenyl group, 1-methyl-1-propenyl group, 2-methyl-1-propenyl group, 1-methyl-2-propenyl group, and 3-butenyl group.
Example of the term of "alkynyl group" includes ethynyl group, 1-propynyl group, 2-propynyl group, 1-methyl-2-propynyl group, and 2-butynyl group.
Examples of the term of "C1-C4 chain hydrocarbon group {wherein the C1-C4 chain hydrocarbon group may have optionally one or more substituents selected from the group consisting of a C1-C3 alkoxy group and a halogen atom}include perfluoroalkyl group (such as trifluoromethyl group) and 2,2-dichloroethylene group.
Examples of the term of "C1-C3 alkoxy group" include methoxy group, ethoxy group, and propoxy group.
When the present compound has one, or two or more asymmetric centers, each optical isomer and mixtures containing the same in optional ratio thereof are encompassed by the present compound. Also, two kinds of geometric isomers due to carbon-carbon double bond, and mixtures containing the same in optional ratio thereof are also encompassed by the present compound.

Examples of the Embodiment of the present compound include the following compounds.

[Embodiment 1] A present compound wherein $Q^1$ represents $CX^1$, $Q^2$ represents $CX^2$, $Q^2$ represents $CX^3$, and $Q^4$ represents $CX^4$.

[Embodiment 2] The compound according to Embodiment 1 wherein $X^1$, $X^3$ and $X^4$ are identical to or different from each other and each represents a C1-C4 alkyl group, a halogen atom, or a hydrogen atom.

[Embodiment 3] The compound according to Embodiment 1 wherein $X^1$, $X^3$ and $X^4$ are identical to or different from each other and each represents a methyl group, a halogen atom, or a hydrogen atom.

[Embodiment 4] The compound according to Embodiment 1 wherein $X^1$, $X^3$ and $X^4$ represent a hydrogen atom.

[Embodiment 5] The compound according to Embodiment 1 wherein $X^2$ represents a C1-C4 alkyl group which may optionally have one or more halogens, a C1-C4 alkoxy group which may optionally have one or more halogens, a halogen atom, or a hydrogen atom.

[Embodiment 6] The compound according to Embodiment 5 wherein $X^1$, $X^3$ and $X^4$ are identical to or different from each other and each represents a C1-C4 alkyl group, a halogen atom, or a hydrogen atom.

[Embodiment 7] The compound according to Embodiment 5 wherein $X^1$, $X^3$ and $X^4$ are identical to or different from each other, and each represents a methyl group, a halogen atom, or a hydrogen atom.

[Embodiment 8] The compound according to Embodiment 5 wherein $X^1$, $X^3$ and $X^4$ are a hydrogen atom.

[Embodiment 9] The compound according to Embodiment 1 wherein $X^2$ represents a C1-C3 alkyl group which may optionally have one or more fluorine atoms, a C1-C3 alkoxy group which may optionally have one or more fluorine atoms, a halogen atom, or a hydrogen atom.

[Embodiment 10] The compound according to Embodiment 9 wherein $X^1$, $X^3$ and $X^4$ are identical to or different from each other, and each represents a C1-C4 alkyl group, a halogen atom, or a hydrogen atom.

[Embodiment 11] The compound according to Embodiment 9 wherein $X^1$, $X^3$ and $X^4$ are identical to or different from each other, and each represents a methyl group, a halogen atom, or a hydrogen atom.

[Embodiment 12] The compound according to Embodiment 9 wherein $X^1$, $X^3$ and $X^4$ represent a hydrogen atom.

[Embodiment 13] The compound according to Embodiment 1 wherein $X^2$ represents a C1-C3 alkyl group which may optionally have one or more fluorine atoms, a halogen atom, or a hydrogen atom.

[Embodiment 14] The compound according to Embodiment 13 wherein $X^1$, $X^3$ and $X^4$ are identical to or different from each other, and each represents a C1-C4 alkyl group, a halogen atom, or a hydrogen atom.

[Embodiment 15] The compound according to Embodiment 13 wherein $X^1$, $X^3$ and $X^4$ are identical to or different from each other, and each represents a methyl group, a halogen atom, or a hydrogen atom.

[Embodiment 16] The compound according to Embodiment 13 wherein $X^1$, $X^3$ and $X^4$ represent a hydrogen atom.

[Embodiment 17] A present compound wherein $Q^1$ represents a nitrogen atom, $Q^2$ represents $CX^2$, $Q^3$ represents $CX^3$, and $Q^4$ represents $CX^4$.

[Embodiment 18] A present compound wherein $Q^1$ represents a nitrogen atom, $Q^2$ represents CH, $Q^3$ represents CH, and $Q^4$ represents CH.

[Embodiment 19] A present compound wherein $Q^1$ represents $CX^1$, $Q^2$ represents a nitrogen atom, $Q^3$ represents $CX^3$, and $Q^4$ represents $CX^4$.

[Embodiment 20] A present compound wherein $Q^1$ represents CH, $Q^2$ represents a nitrogen atom, $Q^3$ represents CH, and $Q^4$ represents CH.

[Embodiment 21] A present compound wherein $O^1$ represents $CX^1$, $Q^2$ represents $CX^2$, $Q^3$ represents a nitrogen atom, and $Q^4$ represents $CX^4$.

[Embodiment 22] A present compound wherein $Q^1$ represents CH, $Q^2$ represents CH, $Q^3$ represents a nitrogen atom, and $Q^4$ represents CH.

[Embodiment 23] A present compound wherein $Q^1$ represents $CX^1$, $Q^2$ represents $CX^2$, $Q^3$ represents $CX^3$, and $Q^4$ represents a nitrogen atom.

[Embodiment 24] A present compound wherein $Q^1$ represents CH, $Q^2$ represents CH, $Q^3$ represents CH, and $Q^4$ represents a nitrogen atom.

[Embodiment 25] The compound according to any one of Embodiment 1 to Embodiment 24 wherein $R^{21}$, $R^{22}$, $R^{31}$, and $R^{32}$ are identical to or different from each other, and each represents a C1-C3 alkyl group, a halogen atom, or a hydrogen atom.

[Embodiment 26] The compound according to any one of Embodiment 1 to Embodiment 24 wherein $R^{21}$, $R^{22}$, $R^{31}$, and $R^{32}$ are identical to or different from each other, and each represents a methyl group, a halogen atom, or a hydrogen atom.

[Embodiment 27] The compound according to any one of Embodiment 1 to Embodiment 24 wherein $R^{21}$, $R^{22}$, $R^{31}$, and $R^{32}$ are identical to or different from each other, and each represents a methyl group, a fluorine atom, or a hydrogen atom.

[Embodiment 28] The compound according to any one of Embodiment 1 to Embodiment 24 wherein $R^1$ represents a C1-C3 alkyl group or a hydrogen atom.

[Embodiment 29] The compound according to any one of Embodiment 1 to Embodiment 24 wherein $R^1$ represents a C1-C3 alkyl group or a hydrogen atom, and $R^{21}$, $R^{22}$, $R^{31}$, and $R^{32}$ are identical to or different from each other, and each represents a C1-C3 alkyl group, a halogen atom, or a hydrogen atom.

[Embodiment 30] The compound according to any one of Embodiment 1 to Embodiment 24 wherein $R^1$ represents a C1-C3 alkyl group or a hydrogen atom, and $R^{21}$, $R^{22}$, $R^{31}$, and $R^{32}$ represent a methyl group, a halogen atom, or a hydrogen atom.

[Embodiment 31] The compound according to any one of Embodiment 1 to Embodiment 24 wherein $R^1$ represents a C1-C3 alkyl group or a hydrogen atom, and $R^{21}$, $R^{22}$, $R^{31}$, and $R^{32}$ are identical to or different from each other, and each represents a methyl group, a fluorine atom, or a hydrogen atom.

[Embodiment 32] The compound according to any one of Embodiment 1 to Embodiment 24 wherein $R^1$ represents a methyl group or a hydrogen atom.

[Embodiment 33] The compound according to any one of Embodiment 1 to Embodiment 24 wherein $R^1$ represents a methyl group or a hydrogen atom, and $R^{21}$, $R^{22}$, $R^{31}$, and $R^{32}$ are identical to or different from each other, and each represents a C1-C3 alkyl group, a halogen atom, or a hydrogen atom.

[Embodiment 34] The compound according to any one of Embodiment 1 to Embodiment 24 wherein $R^1$ represents a methyl group or a hydrogen atom, and $R^{21}$, $R^{22}$, $R^{31}$, and $R^{32}$ are identical to or different from each other, and each represents a methyl group, a halogen atom, or a hydrogen atom.

[Embodiment 35] The compound according to any one of Embodiment 1 to Embodiment 24 wherein $R^1$ represents a methyl group or a hydrogen atom, and $R^{21}$, $R^{22}$, $R^{31}$, and $R^{32}$ are identical to or different from each other, and each represents a methyl group, a fluorine atom, or a hydrogen atom.

Next, a process for preparing the present compound is explained.

Process 1

The present compound can be prepared according to a step wherein the compound represented by formula (II-a) (hereinafter, referred to as "Compound (II-a)") and a compound represented by formula (R-1) (hereinafter, referred to as "Compound (R-1)" in the presence of a base to a product (hereinafter, referred to as "crude product (1)) (hereinafter, the step may be referred to as "Step (1)", and a step wherein the crude product (1) and a compound represented by formula (R-2) (hereinafter, referred to as "Compound (R-2)") are reacted in the presence of a base (hereinafter, the step may be referred to as "Step (2)".

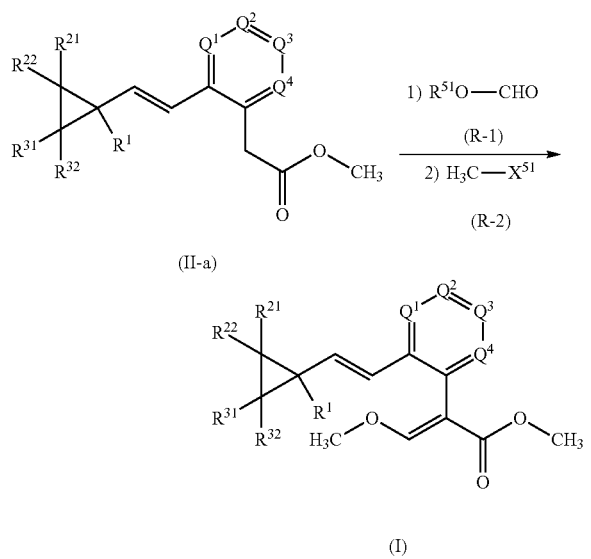

[wherein $R^{51}$ represents a C1-C4 alkyl group, $X^{51}$ represents a chlorine atom, a bromine atom, an iodine atom, a C1-C4 alkoxysulfonyloxy group, a C1-C4 alkanesulfonyloxy group, or a tosyloxy group, and the other symbols are the same as those defined above]

The C1-C4 alkoxy sulfonyloxy group and the C1-C4 alkanesulfonyloxy group represents a group which functions as a leaving group, and includes, for example, a methanesulfonyloxy group and a trifluoromethanesulfonyloxy group.

The step (1) is usually carried out in a solvent. Examples of the solvent to be used in the reaction include ethers such as diethyl ether, ethylene glycol dimethyl ether, methyl tert-butyl ether (hereinafter, referred to as "MTBE"), tetrahydrofuran (hereinafter, referred to as "THF") (hereinafter, collectively referred to as "ethers"); aprotic polar solvents (such as dimethyl formamide (hereinafter, referred to as "DMF"), N-methylpyrrolidone, dimethyl sulfoxide (hereinafter, referred to as "DMSO") (hereinafter, collectively referred to as "aprotic polar solvents", and mixed solvents of these two or more solvents.

Examples of the bases to be used in the reaction include alkali metal hydrides (such as sodium hydride, potassium hydride) (hereinafter, collectively referred to as "alkali metal hydrides").

In the reaction, the compound (R-1) is used usually within a range of 1 to 10 molar ratio(s), and the base is used usually within a range of 0.5 to 5 molar ratios, relative to 1 mole of the compound (II-a).

The reaction period of the reaction is usually within 5 minutes to 72 hours. The reaction temperature is usually within a range of −20 to 100° C.

When the reaction is completed, water is added to the reaction mixture, the reaction mixture is extracted with organic solvent(s), and the resulting organic layer is worked up (for example, drying and concentration) to obtain the crude product (1).

The compound (R-1) is a commercially available compound, or may be prepared according to a publicly known method.

The step (2) is usually carried out in a solvent. Examples of the solvent to be used in the reaction include ethers; aprotic polar solvents, and mixed solvents of these two or more solvents.

Examples of the bases to be used in the reaction include alkali metal hydrides; alkali metal carbonates (such as sodium carbonates, and potassium carbonates) (hereinafter, referred to "alkali metal carbonates").

In the reaction, the compound (R-2) is used usually within a range of 1 to 10 molar ratio(s), and the base is used usually within a range of 1 to 5 molar ratio(s), relative to 1 mole of the compound (II-a) which is used in the step (1).

The reaction period of the reaction is usually within 5 minutes to 72 hours. The reaction temperature is usually within a range of −20 to 100° C.

When the reaction is completed, water is added to the reaction mixture, the reaction mixture is extracted with organic solvent(s), and the resulting layer is worked up (for example, drying and concentration) to isolate the present compound.

The compound (R-2) is a commercially available compound, or may be prepared according to a publicly known method.

Process 2

The present compound can be prepared by reacting a compound represented by formula (III-a) (hereinafter, referred to as "Compound (III-a)") and a compound represented by formula (R-3) (hereinafter, referred to as "Compound (R-3)") in the presence of a catalyst and a base.

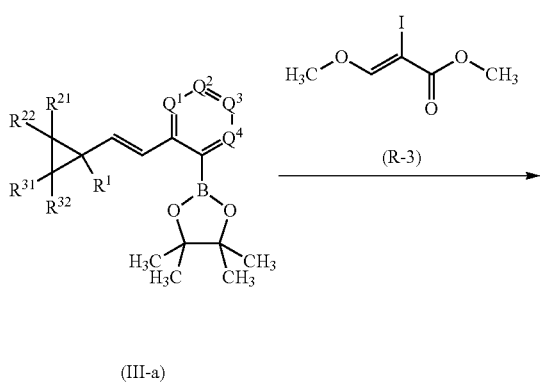

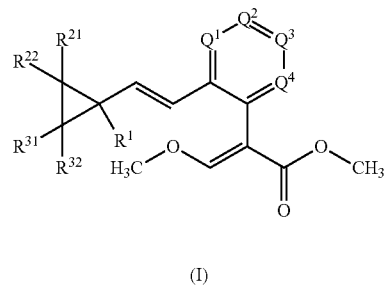

(I)

[wherein the symbols are the same as those defined above]

The reaction is usually carried out in a solvent. Examples of the solvent to be used in the reaction include hydrocarbons such as hexane, toluene and xylene (hereinafter, collectively referred to as "hydrocarbons"); ethers; halogenated hydrocarbons (such as chloroform and chlorobenzene) (hereinafter, collectively referred to as to "halogenated hydrocarbons"); aprotic polar solvents; esters (such as ethyl acetate) (hereinafter, collectively referred to as "esters"); and mixed solvents of these two or more solvents.

Examples of the base to be used in the reaction include alkali metal carbonates (such as sodium carbonate and potassium carbonate); alkali metal phosphates (such as tripotassium phosphates) (hereinafter, collectively referred to as "phosphates"); and acetates (such as sodium acetate) (hereinafter, collectively referred to as "acetates").

Examples of the catalyst to be used in the reaction include palladium catalyst (such as tetrakis(triphenylphosphine)palladium (0), [1,1'-bis(diphenylphoshino)ferrocene]palladium (II) dichloride dichloromethane adducts and so on.

In the reaction, the compound (R-3) is used usually within a range of 1 to 10 molar ratio(s), the catalyst is used usually within a range of 0.0001 to 1 molar ratio(s), and the base is used usually within a range of 0.1 to 5 molar ratio(s), relative to 1 mole of the compound (III-a).

The reaction period is usually within a range of 5 minutes to 72 hours. The reaction temperature is usually within a range of 0 to 150° C.

When the reaction is completed, water is added to the reaction mixtures, and the reaction mixtures are extracted with organic solvent(s), and the resulting organic layers are worked up (for example, drying and concentration) to isolate the present compound.

The compound (R-3) is a commercially available compound.

Reference Process 1

The compound (II-a) can be prepared by reacting a compound represented by formula (IV-a) (hereinafter, referred to as "Compound (IV-a)") with a compound represented by formula (R-4) (hereinafter, referred to as "Compound (R-4)") in the presence of a catalyst and a base.

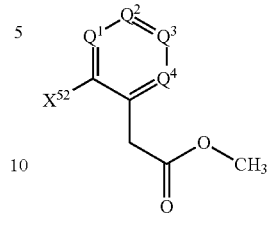

(IV-a)

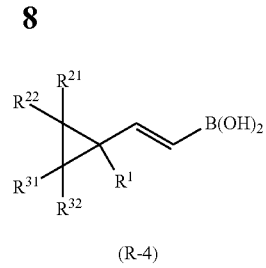

(R-4)

(II-a)

[wherein $X^{52}$ represents a chlorine atom, a bromine atom, an iodine atom, or a trifluoromethasulfonyloxy group, and the other symbols are the same as those defined above.]

The reaction can be carried out by using the compound (R-4) in place of the compound (III-a) and the compound (IV-a) in place of the compound (R-3) according to the Process 2.

The compound (IV-a) and the compound (R-4) are commercially available compound, or may be prepared according to a publicly known method.

Reference Process 2

The compound (III-a) can be prepared by reacting a compound represented by formula (V-a) (hereinafter, referred to "Compound (V-a)") with bis(pinacolato)diboron in the presence of a catalyst and a base.

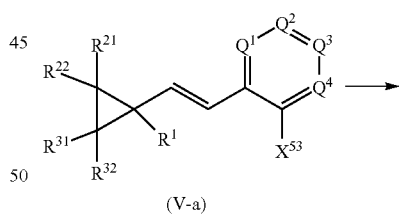

(V-a)

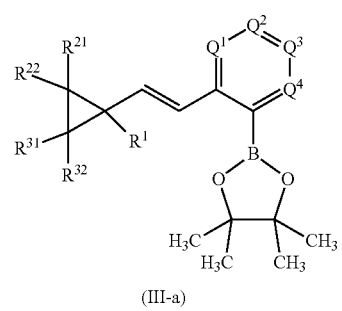

(III-a)

Wherein $X^{53}$ represents a bromine atom, an iodine atom or a trifluoromethansulfonyl group, and the other symbols have the same as defined above.]

The reaction can be carried out by using bis(pinacolato)diboron in place of the compound (III-a) and the compound (V-a) in place of the compound (R-3) according to the Process 2.

Reference Process 3

The compound (III-a) can be prepared by reacting a compound represented by formula (V-b) (that is, the compound (V-a) wherein $X^{53}$ represents an iodine atom; hereinafter, referred to as "Compound (V-b)") with pinacolborane in the presence of a catalyst and a base.

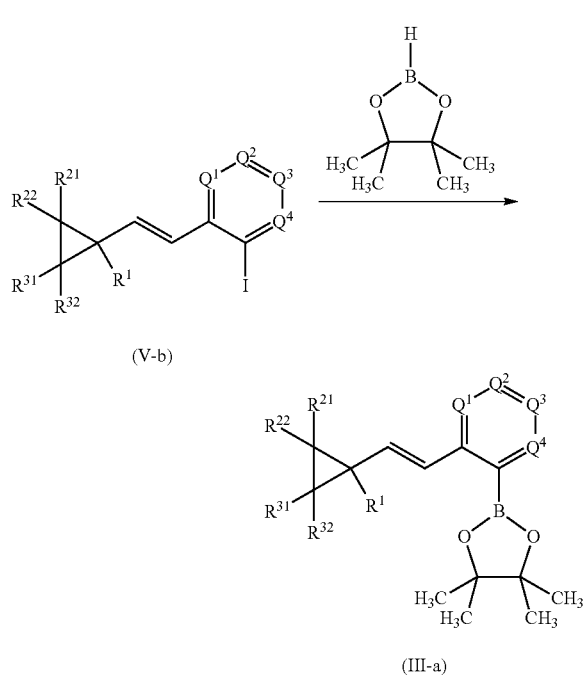

[wherein the symbols are the same as those defined above]

The reaction is usually carried out in a solvent. Examples of the solvent to be used in the reaction include hydrocarbons; ethers; halogenated hydrocarbons; aprotic polar solvents; esters; and mixed solvents of these two or more solvents.

Examples of the base to be used in the reaction include alkali metal hydrides.

Examples of the catalyst to be used in the reaction include copper (I) iodide.

In the reaction, pinacolborane is used usually within a range of 1 to 10 molar ratio(s), the catalyst is used usually within a range of 0.01 to 1 molar ratio(s), and the base is used usually within a range of 1 to 5 molar ratio(s), relative to 1 mole of the compound (V-b).

The reaction period is usually within a range of 5 minutes to 72 hours. The reaction temperature is usually within a range of −20 to 100° C.

When the reaction is completed, water is added to the reaction mixture, the reaction mixtures are extracted with organic solvent(s), the resulting organic layers are worked up (for example, drying and concentration) to isolate Compound (III-a).

Reference Process 4

The compound (V-c) can be prepared by reacting a compound represented by formula (VIII-a) (hereinafter, referred to as "Compound (VIII-a)") with trifluoromethane sulfonic anhydride in the presence of a base.

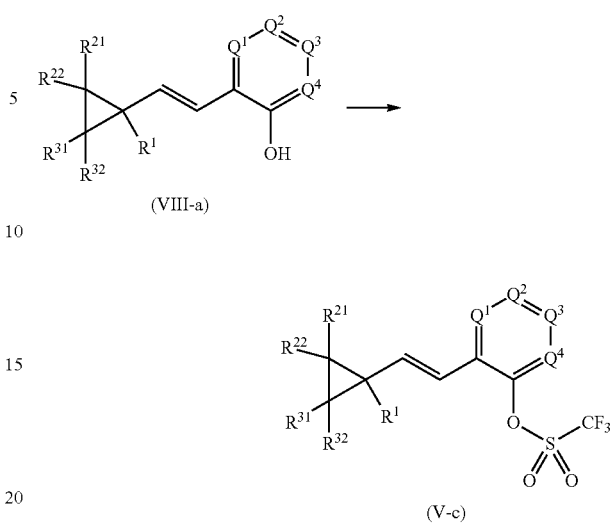

[wherein the symbols are the same as those defined above]

The reaction is usually carried out in a solvent. Examples of the solvents to be used in the reaction include hydrocarbons; ethers; halogenated hydrocarbons; esters; and mixed solvents of these two or more solvents.

Examples of the base to be used in the reaction include organic bases such as triethyl amine and pyridine (hereinafter, referred to as "Organic bases").

In the reaction, trifluorometansulfonic anhydride is used usually within a range of 1 to 5 molar ratio(s), and the base is used usually within a range of 1 to 50 molar ratio(s), relative to 1 mole of the compound (VIII-a).

The reaction period is usually within a range of 5 minutes to 72 hours. The reaction mixture is usually within a range of −20 to 100° C.

When the reaction is completed, water is added to reaction mixtures, and the resulting mixtures are worked up (for example, drying and concentration) to isolate Compound (V-c).

Reference Process 5

The compound (V-a) can be prepared by reacting a compound represented by formula (VI-a) (hereinafter, referred to as "Compound (VI-a)") with a compound represented by formula (VII-a) (hereinafter, referred to as "Compound (VII-a)") in the presence of a base.

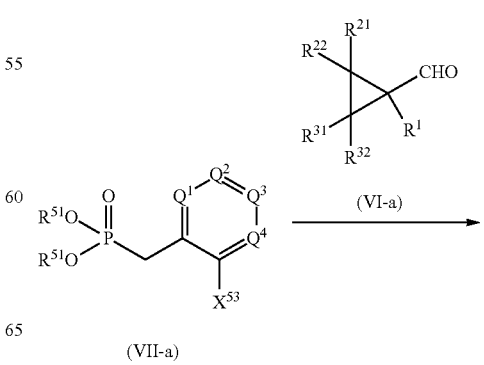

-continued

[Structure (V-a) with substituents $R^{21}$, $R^{22}$, $R^{31}$, $R^{32}$, $R^1$, $Q^1$, $Q^2$, $Q^3$, $Q^4$, $X^{53}$]

(V-a)

[wherein the symbols are the same as those defined above]

The reaction is usually carried out in a solvent. Examples of the solvents to be used in the reaction include hydrocarbons; ethers; halogenated hydrocarbons; aprotic polar solvents; and mixed solvents of these two or more solvents.

Examples of the bases to be used in the reaction include alkaline metal alkoxides (such as potassium tert-butoxide) (hereinafter, collectively referred to as "alkaline metal alkoxides").

In the reaction, the compound (VI-a) is used usually within a range of 0.5 to 5 molar ratio(s), and the base is used usually within a range of 1 to 5 molar ratio(s), relative to 1 mole of the compound (VII-a).

Lithium chloride may be used in the reaction as needed. When lithium chloride is used in the reaction, lithium chloride is used usually within a range of 0.01 to 10 molar ratio(s) relative to 1 mole of the compound (VII-a).

The reaction period is usually within a range of 5 minutes to 72 hours. The reaction temperature is usually within a range of −20 to 100° C.

When the reaction is completed, water is added to the reaction mixtures, the reaction mixtures are extracted with organic solvent(s), and the resulting organic layers are worked up (for example, drying and concentration) to isolate Compound (V-a).

The compound (VII-a) is a commercially available compound, or may be prepared according to a publicly known method.

Reference Process 6

The compound (VI-a) can be prepared by reacting a compound represented by formula (IX-a) (hereinafter, referred to as "Compound (IX-a)") with a reducing agent.

[Structures (IX-a) → (VI-a)]

[wherein the symbols are the same as those defined above]

The reaction is usually carried out in a solvent. Examples of the solvents to be used in the reaction include hydrocarbons; halogenated hydrocarbons; and mixed solvents of two or more of these solvents.

Examples of the reducing agent include diisobutylaluminium hydride.

In the reaction, the reducing agent is used usually within a range of 1 to 2 molar ratio(s) relative to 1 mole of the compound (IX-a).

The reaction period is usually within a range of 5 minutes to 10 hours. The reaction temperature is usually within a range of −20 to 20° C.

When the reaction is completed, water is added to the reaction mixtures, the reaction mixtures are extracted with organic solvent(s), and the resulting organic layers are worked up (for example, drying and concentration) to isolate Compound (VI-a). Alternatively, the organic layers may be used as itself without concentration to the Reference process 5.

Reference Process 7

The compound (IX-a) can be prepared by reacting a compound represented by formula (IX-b) (hereinafter, referred to as "Compound (IX-b)") with N,O-dimethyl hydroxylamine in the presence of a condensing agent.

[Structures (IX-b) → (IX-a)]

[wherein the symbols are the same as those defined above]

The reaction is usually carried out in a solvent. Examples of the solvents to be used in the reaction include hydrocarbons; and halogenated hydrocarbons; and mixed solvents of these two or more solvents.

Examples of the condensing agent to be used in the reaction include N,N'-diisopropyl carbodiimide.

N,O-Dimethyl hydroxylamine may be used as its hydrochloride salt or sulfate salt.

In the reaction, N,O-dimethyl hydroxylamine is used usually within a range of 1 to 10 molar ratio(s), and the condensing agent is used usually within a range of 1 to 10 molar ratio(s), relative to 1 mole of the Compound (IX-b).

A base and/or 1-hydroxy benzotriazole may be used in the reaction as needed. Examples of the base include organic bases. When the base is used in the reaction, the base is used usually within a range of 1 to 10 molar ratio(s) relative to 1 mole of the compound (IX-b). When 1-hydroxybenzotriazole is used in the reaction, 1-hydroxybenzotriazole is used usually within a range of 0.001 to 1 molar ratio(s) relative to 1 mole of the compound (IX-b).

The reaction period is usually within a range of 5 minutes to 10 hours. The reaction temperature is usually within a range of −20 to 100° C.

When the reaction is completed, water is added to the reaction mixtures, the reaction mixtures are extracted with organic solvent(s), and the resulting organic layers are worked up (for example, drying and concentration) to isolate Compound (IX-a).

Reference Process 8

The compound (VIII-a) can be prepared by reacting a compound represented by formula (X-a) (hereinafter, referred to as "Compound (X-a)") with a base.

[Structure (X-a)]

-continued

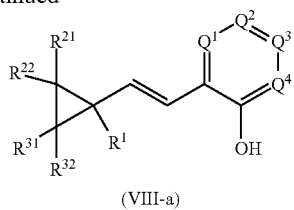

(VIII-a)

[wherein the symbols are the same as those defined above]

The reaction is usually carried out in a solvent. Examples of the solvents to be used in the reaction include hydrogen carbons; ethers; halogenated hydrogen carbons; esters; water; and mixed solvents of these two or more solvents.

Examples of the base to be used in the reaction include tetrabutyl ammonium fluoride and tripotassium phosphate.

In the reaction, the base is used usually within a range of 1 to 50 molar ratio(s) relative to 1 mole of the compound (X-a).

The reaction period is usually within a range of 5 minutes to 72 hours. The reaction temperature is usually within a range of −20 to 100° C.

When the reaction is completed, water is added to the reaction mixtures, the reaction mixtures are extracted with organic solvent(s), and the resulting organic layers are worked up (for example, drying and concentration) to isolate Compound (VIII-a).

Reference Process 9

The compound (X-a) can be prepared by reacting a compound represented by formula (XI-a) (hereinafter, referred to as "Compound (XI-a)") with the compound (R-4) in the presence of a catalyst and a base.

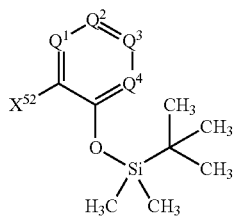

(XI-a)

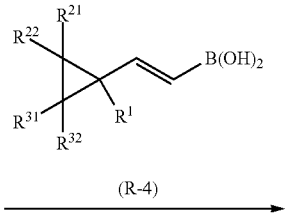

(R-4)

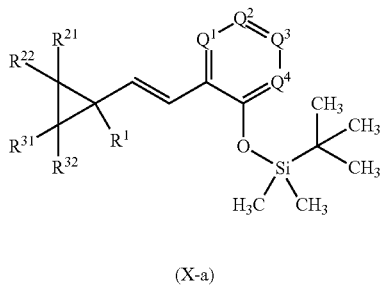

(X-a)

[wherein the symbols are the same as those defined above]

The reaction can be carried out by using the compound (XI-a) in place of the compound (IV-a) according to the Reference Process 1.

The compound (XI-a) can be prepared according to a publicly known method.

Reference Process 10

The compound (VIII-a) can be prepared by reacting a compound represented by formula (XII-a) (hereinafter, referred to as "Compound (XII-a)") with methanol in the presence of an acid.

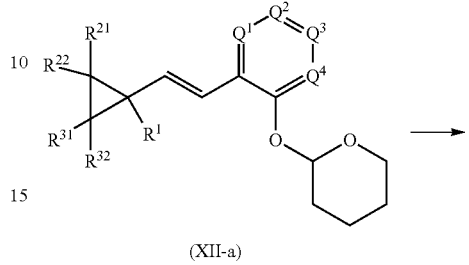

(XII-a)

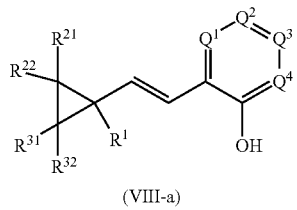

(VIII-a)

[wherein the symbols are the same as those defined above]

The reaction is usually carried out in a solvent. Examples of the solvent to be used in the reaction include alcohols such as methanol; water; and mixed solvents of these two or more solvents.

Examples of acid to be used in the reaction include hydrochloric acid and p-toluenesulfonic acid.

In the reaction, methanol is used usually within a range of 1 to 10 molar ratio(s) and the acid is used usually within a range of 0.001 to 0.1 molar ratios, relative to 1 mole of the compound (XII-a).

The reaction period is usually within a range of 5 minutes to 72 hours. The reaction temperature is usually within a range of −20 to 100° C.

When the reaction is completed, water is added to the reaction mixtures, the reaction mixtures are extracted with organic solvent(s), and the resulting organic layers are worked up (for example, drying and concentration) to isolate Compound (VIII-a).

Reference Process 11

The compound (XII-a) can be prepared by reacting a compound represented by formula (XIII-a) (hereinafter, referred to as "Compound (XIII-a)") with the compound (R-4) in the presence of a catalyst and a base.

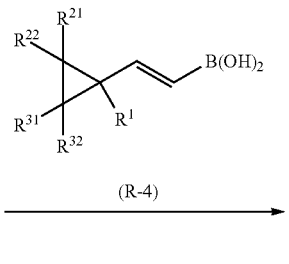

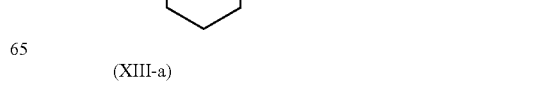

(XIII-a) (R-4)

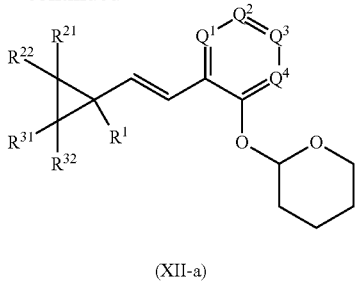

(XII-a)

[wherein the symbols are the same as those defined above]

The reaction can be carried out by using the compound (XIII-a) in place of the compound (IV-a) according to the Reference Process 1.

The compound (XIII-a) can be prepared according to a publicly known method.

The present compound has control effect on harmful arthropods such as harmful insects and harmful mites, harmful mollusks, and harmful nematodes. Examples of the harmful arthropods, harmful mollusks, and harmful nematodes include the followings.

Hemiptera:

from the family Delphacidae, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), *Tagosodes oryzicolus*, and the like; from the family Cicadellidae, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and the like;

from the family Cercopidae, *Mahanarva posticata*, *Mahanarva fimbriolata*, and the like;

from the family Aphididae, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and the like;

from the family Phylloxeridae, grapevine phylloxera (*Daktulosphaira vitifoliae*), Pecan phylloxera (*Phylloxera devastatrix*), Pecan leaf phylloxera (*Phylloxera notabilis*), Southern pecan leaf phylloxera (*Phylloxera russellae*), and the like;

from the family Adelgidae, hemlock woolly aphid (*Adelges tsugae*), *Adelges piceae*, *Aphrastasia pectinatae*, and the like;

from the family Pentatomidae, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, *Dichelops melacanthus*, and the like;

from the family Cydnidae, Burrower brown bug (*Scaptocoris castanea*);

from the family Alydidae, for example, bean bug (*Riptortus pedestris*), corbett rice bug (*Leptocorisa chinensis*), rice bug (*Leptocorisa acuta*), and the like;

from the family Coreidae, *Cletus punctiger*, Australian leaf-footed bug (*Leptoglossus australis*), and the like;

from the family Lygaeidae, oriental chinch bug (*Caverelius saccharivorus*), seed bug (*Togo hemipterus*), chinch bug (*Blissus leucopterus*), and the like;

from the family Miridae, rice leaf bug (*Trigonotylus caelestialium*), sorghum plant bug (*Stenotus rubrovittatus*), wheat leaf bug (*Stenodema calcarata*), American tarnished plant bug (*Lygus lineolaris*), and the like;

from the family Aleyrodidae, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), *Pealius euryae*, and the like;

from the family Diaspididae, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), citrus snow scale (*Unaspis citri*), and the like;

from the family Coccidae, pink wax scale (*Ceroplastes rubens*);

from the family Margarodidae, fluted scale (*Icerya purchasi*) seychelles fluted scale (*Icerya seychellarum*), and the like;

from the family Pseudococcidae, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), tuttle mealybug (*Brevennia rehi*), and the like;

from the family Psyllidae, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), Pear psylla (*Cacopsylla pyricola*), and the like;

from the family Tingidae, sycamore lace bug (*Corythucha ciliata*), aster tingid (*Corythucha marmorata*), Japanese pear lace bug (*Stephanitis nashi*), azalea lace bug (*Stephanitis pyrioides*), and the like;

from the family Cimicidae, common bed bug (*Cimex lectularius*), tropical bed bug (*Cimex lectularius*), and the like;

from the family Cicadidae, Giant Cicada (*Quesada gigas*), and the like;

from the family Reduviidae, *Triatoma infestans*, *Rhodonius prolixus*, and the like;

*Triatoma* spp.

Lepidoptera:

from the family Crambidae, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha*

*derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), Sugarcane borer (*Diatraea saccharalis*), and the like;

from the family Pyralidae, lesser cornstalk borer (*Elasmopalpus lignosellus*), mealworm moth (*Plodia interpunctella*), persimmon bark borer (*Euzophera batangensis*), fig moth (*Cadra cautella*), and the like;

from the family Noctuidae, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), Velvetbean caterpillar (*Anticarsia gemmatalis*), Cotton leafworm (*Alabama argillacea*), Hop vine borer (*Hydraecia immanis*), and the like;

from the family Pieridae, common cabbage worm (*Pieris rapae*), and the like;

from the family Tortricidae, oriental fruit moth (*Grapholita molesta*), *Grapholita dimorpha*, soybean moth (*Leguminivora glycinivorella*), Matsumuraeses azukivora, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), Bean Shoot Borer (*Epinotia aporema*), Citrus fruit borer (*Ecdytolopha aurantiana*), and the like;

from the family Gracillariidae, tea leaf roller (*Caloptilia theivora*), Asiatic apple leaf miner (*Phyllonorycter ringoniella*), and the like;

from the family Carposinidae, peach fruit moth (*Carposina sasakii*), and the like;

from the family Lyonetiidae, Coffee Leaf miner (*Leucoptera coffeella*), peach leaf miner (*Lyonetia clerkella*), *Lyonetia prunifoliella*, and the like;

from the family Lymantriidae, *Lymantria* spp. (such as gypsy moth (*Lymantria dispar*)), *Euproctis* spp. (such as tea lymantriid (*Euproctis pseudoconspersa*)), and the like;

from the family Plutellidae, diamondback moth (*Plutella xylostella*), and the like;

from the family Gelechiidae, peach worm (*Anarsia lineatella*), sweetpotato leaf folder (*Helcystogramma triannulella*), pink bollworm (*Pectinophora gossypiella*), potato moth (*Phthorimaea operculella*), *Tuta absoluta*, and the like;

from the family Arctiidae, American white moth (*Hyphantria cunea*), and the like;

from the family Castniidae, Giant Sugarcane borer (*Telchin licus*), and the like;

from the family Cossidae, *Cossus insularis*, and the like;
from the family Geometridae, *Ascotis selenaria*, and the like;

from the family Limacodidae, blue-striped nettle grub (*Parasa lepida*), and the like;

from the family Stathmopodidae, persimmon fruit moth (*Stathmopoda masinissa*), and the like;

from the family Sphingidae, tobacco hornworm (*Acherontia lachesis*), and the like;

from the family Sesiidae, *Nokona feralis*, cherry borer (*Synanthedon hector*), *Synanthedon tenuis*, and the like:

from the family Hesperiidae, rice skipper (*Parnara guttata*), and the like;

from the family Tineidae, casemaking clothes moth (*Tinea translucens*), common clothes moth (*Tineola bisselliella*), and the like.

Thysanoptera:

from the family Thripidae, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), *Echinothrips americanus*, and the like;

from the family Phlaeothripidae, aculeated rice thrips (*Haplothrips aculeatus*), and the like.

Diptera:

from the family Anthomyiidae, seedcorn maggot (*Delia platura*), onion maggot (*Delia antiqua*), beet leaf miner (*Pegomya cunicularia*), and the like;

from the family Ulidiidae, sugarbeet root maggot (*Tetanops myopaeformis*), and the like;

from the family Agromyzidae, rice leaf miner (*Agromyza oryzae*), tomato leaf miner (*Liriomyza sativae*), chrysanthemum leaf miner (*Liriomyza trifolii*), pea leafminer (*Chromatomyia horticola*), and the like;

from the family Chloropidae, rice stem maggot (*Chlorops oryzae*), and the like;

from the family Tephritidae, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), Japanese cherry fruit fly (*Rhacochlaena japonica*), and the like;

from the family Ephydridae, smaller rice leaf miner (*Hydrellia griseola*), whorl maggot (*Hydrellia philippina*), paddy stem maggot (*Hydrellia sasakii*), and the like;

from the family Drosophilidae, cherry drosophila (*Drosophila suzukii*), and the like;

from the family Phoridae, *Megaselia spiracularis*, and the like;

from the family Psychodidae, *Clogmia albipunctata*, and the like;

from the family Sciaridae, *Bradysia difformis*, and the like;

from the family Cecidomyiidae, hessian fly (*Mayetiola destructor*), paddy gall fly (*Orseolia oryzae*), and the like;

from the family Diopsidae, *Diopsis macrophthalma*, and the like;

from the family Tipulidae, rice crane fly (*Tipula aino*), Common cranefly (*Tipula oleracea*), European cranefly (*Tipula paludosa*), and the like;

from the family Culicidae, southern house mosquito (*Culex pipiens pallens*), *Culex tritaeniorhynchus*, *Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae*, *Anopheles stephensi*, *Anopheles coluzzii*, *Anopheles albimanus*, *Anopheles sundaicus*, *Anopheles arabiensis*, *Anopheles funestus*, *Anopheles darlingi*, *Anopheles farauti*, *Anopheles minimus*, and the like;

from the family Simulidae, *Prosimulium yezoensis*, *Simulium ornatum*, and the like;

from the family Tabanidae, *Tabanus trigonus*, and the like;

from the family Muscidae, house fly (*Musca domestica*), false stable fly (*Muscina stabulans*), biting house fly (*Stomoxys calcitrans*), buffalo fly (*Haematobia irritans*) and the like;

from the family Calliphoridae;

from the family Sarcophagidae;

from the family Chironomidae, *Chironomus plumosus*, *Chironomus yoshimatsui*, *Glyptotendipes tokunagai*, and the like;

from the family Fannidae.

Coleoptera:

from the family Chrysomelidae, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, tobacco flea beetle (*Epitrix hirtipennis*), and the like;

from the family Carabidae, Seedcorn beetle (*Stenolophus lecontei*), Slender seedcorn beetle (*Clivina impressifrons*), and the like;

from the family Scarabaeidae, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus*, *Holotrichia* spp., *Phyllophaga* spp. (such as June beetle (*Phyllophaga crinita*)), and *Diloboderus* spp. (such as *Diloboderus abderus*), and the like;

from the family Curculionidae, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), cotton root borer (*Eutinobothrus brasiliensis*), and the like;

from the family Tenebrionidae, red meal beetle (*Tribolium castaneum*), mason beetle (*Tribolium confusum*), lesser mealworm (*Alphitobius diaperinus*), and the like;

from the family Coccinellidae, twenty-eight-spotted ladybird (*Epilachna vigintioctopunctata*), and the like;

from the family Bostrychidae, common powder-post beetle (*Lyctus brunneus*), lesser grain borer (*Rhizopertha dominica*), and the like;

from the family Ptinidae;

from the family Cerambycidae, citrus long-horned beetle (*Anoplophora malasiaca*), *Migdolus fryanus*, and the like;

from the family Elateridae, *Melanotus okinawensis*, barley wireworm (*Agriotes fuscicollis*), *Melanotus legatus*, *Anchastus* spp., *Conoderus* spp., *Ctenicera* spp., *Limonius* spp., *Aeolus* spp., and the like;

from the family Staphylinidae, *Paederus fuscipes*, and the like;

from the family Dermestidae, varied carpet beetle (*Anthrenus verbasci*), hide beetle (*Dermestes maculates*), khapra beetle (*Trogoderma granarium*), and the like;

from the family Anobidae, tobacco beetle (*Lasioderma serricorne*) and biscuit beetle (*Stegobium paniceum*), and the like;

from the family Laemophloeidae, flat grain beetle (*Cryptolestes ferrugineus*), and the like;

from the family Silvanidae, saw-toothed grain beetle (*Oryzaephilus surinamensis*), and the like.

Orthoptera:

from the family Acrididae, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*) Japanese grasshopper (*Oxya yezoensis*), rice grasshopper (*Oxya japonica*), Bombay locust (*Patanga succincta*), and the like;

from the family Gryllotalpidae, oriental mole cricket (*Gryllotalpa orientalis*), and the like;

from the family Gryllidae, house cricket (*Acheta domestica*), emma field cricket (*Teleogryllus emma*), and the like;

from the family Tettigoniidae, for example, Mormon cricket (*Anabrus simplex*), and the like.

Hymenoptera:

from the family Tenthredinidae, beet sawfly (*Athalia rosae*), nippon cabbage sawfly (*Athalia japonica*), and the like;

from the family Formicidae, *Solenopsis* spp. (such as red imported fire ant (*Solenopsis invicta*), tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica fusca japonica*, *Pristomyrmex punctutus*, *Pheidole noda*, big-headed ant (*Pheidole megacephala*), *Camponotus* spp. (such as *Camponotus japonicus*, *Camponotus obscuripes*), *Pogonomyrmex* spp. (such as western harvester ant (*Pogonomyrmex occidentalis*)), *Wasmania* spp. (such as *Wasmania auropunctata*), long-legged ant (*Anoplolepis gracilipes*), and the like;

from the family Vespidae, Asian giant hornet (*Vespa mandarinia japonica*), *Vespa simillima*, *Vespa analis Fabriciusi*, Asian hornet (*Vespa velutina*), *Polistes jokahamae*, and the like;

from the family Siricidae, pine wood wasp (*Urocerus gigas*), and the like;

from the family Bethylidae.

Blattodea:
  from the family Blattellidae, German cockroach (*Blattella germanica*), and the like;
  from the family Blattidae, smoky-brown cockroach (*Periplaneta fuliginosa*), American cockroach (*Periplaneta americana*), brown cockroach (*Periplaneta brunnea*), black cockroach (*Blatta orientalis*), and the like;
  from the family Termitidae, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae, Cornitermes cumulans*, and the like.
Siphonaptera:
  *Pulex* spp. (such as human flea (*Pulex irritans*)), *Ctenocephalides* spp. (such as cat flea (*Ctenocephalides felis*), dog flea (*Ctenocephalides canis*)), *Xenopsylla* spp. (such as oriental rat flea (*Xenopsylla cheopis*)), *Tunga* spp. (such as chigoe flea (*Tunga penetrans*)), *Echidnophaga* spp. (such as chicken flea (*Echidnophaga gallinacea*)), *Nosopsyllus* spp. (such as European rat flea (*Nosopsyllus fasciatus*)).
Psocodae:
  *Pediculus* spp. (such as head louse (*Pediculus humanus capitis*)); *Phtirus* spp. (such as crab louse (*Pthirus pubis*)); *Haematopinus* spp. (such as short-nosed cattle louse (*Haematopinus eurysternus*), pig louse (*Haematopinus suis*)); *Damalinia* spp. (such as *Dalmalinia ovis, Damalinia bovis*); *Linognathus* spp. (such as blue cattle louse (*Linognathus vituli*), sheep face louse (*Linognathus ovillus*)); *Solenopotes* spp. (such as capillate louse (*Solenopotes capillatus*)); *Menopon* spp. (such as common chicken louse (*Menopon gallinae*)); *Trimenopon* spp.; *Trinoton* spp.; *Trichodectes* spp. (such as dog biting louse (*Trichodectes canis*)); *Felicola* spp. (such as cat louse (*Felicola subrostratus*)); *Bovicola* spp. (such as cattle biting louse (*Bovicola bovis*)); *Menacanthus* spp. (such as chicken body louse (*Menacanthus stramineus*)); *Werneckiella* spp.; *Lepikentron* spp.;
  from the family Liposcelididae, book louse (*Liposcelis subfuscas*), *Liposcelis bostrychophilus, Liposcelis simulans, Liposcelis divinatorius, Liposcelis entomophila*, and the like.
Thysanura:
  from the family Lepismatidae, oriental silverfish (*Ctenolepisma villosa*), moth fish (*Lepisma saccharina*), and the like.
Acari:
  from the family Tetranychidae, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), *Oligonychus* spp., and the like;
  from the family Eriophyidae, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri, Aceria tosichella, Shevtchenkella* sp., and the like;
  from the family Tarsonemidae, broad mite (*Polyphagotarsonemus latus*), and the like;
  from the family Tenuipalpidae, *Brevipalpus phoenicis*, and the like;
  from the family Tuckerellidae;
  from the family Ixodidae, *Haemaphysalis* spp. (such as *Haemaphysalis longicornis, Haemaphysalis flava, Haemaphysalis campanulata*), *Dermacentor* spp. (such as American dog tick (*Dermacentor variabilis*), *Dermacentor taiwanicus*, Rocky Mountain wood tick (*Dermacentor andersoni*)), *Ixodes* spp. (such as *Ixodes ovatus, Ixodes persulcatus*, black-legged tick (*Ixodes scapularis*), *Ixodes pacificus, Ixodes holocyclus*), *Amblyomma* spp. (such as lone star tick (*Amblyomma americanum*), gulf coast tick (*Amblyomma maculatum*)), *Boophilus* spp. (such as *Rhipicephalus* (*Boophilus*) *microplus, Boophilus annulatus*), and *Rhipicephalus* spp. (such as brown dog tick (*Rhipicephalus sanguineus*), *Rhipicephalus appendiculatus*);
  from the family Acaridae, cereal mite (*Tyrophagus putrescentiae*), grassland mite (*Tyrophagus similis*), and the like;
  from the family Pyroglyphidae, American house dust mite (*Dermatophagoides farinae*), European house dust mite (*Dermatophagoides pteronyssinus*), and the like;
  from the family Cheyletidae, *Cheyletus eruditus, Cheyletus malaccensis, Chelacaropsis moorei, Cheyletiella yasguri*, and the like;
  *Argas* spp. (such as fowl tick (*Argas persicus*)), *Ornithodorus* spp. (such as *Ornithodorus hermsi, Ornithodorus turicata*), *Psoroptes* spp. (such as sheep scab mite (*Psoroptes ovis*), horse psoroptic mange mite (*Psoroptes equi*)), *Knemidocoptes* spp. (such as *Knemidocoptes mutans*), *Notoedres* spp. (such as *Notoedres cati, Notoedres muris*), *Sarcoptes* spp. (such as itch mite (*Sarcoptes scabiei*)), *Otodectes* spp. (such as ear mange mite (*Otodectes cynotis*)), *Listrophorus* spp. (such as *Listrophorus gibbus*), *Chorioptes* spp., *Hypodectes* spp., *Pterolichus* spp., *Cytodites* spp., *Laminosioptes* spp., *Dermanyssus* spp. (such as bird mite (*Dermanyssus gallinae*)), *Ornithonyssus* spp. (such as feather mite (*Ornithonyssus sylviarum*), tropical rat mite (*Ornithonyssus bacoti*)), *Varroa* spp. (such as *Varroa jacobsoni*), *Cheyletiella* spp. (such as *Cheyletiella yasguri, Cheyletiella blakei*), *Ornithocheyletia* spp., *Demodex* spp. (such as dog follicle mite (*Demodex canis*), cat follicle mite (*Demodex cati*)), *Myobia* spp., *Psorergates* spp., *Trombicula* spp. (such as *Trombicula akamushi, Trombicula pallida, Trombicula scutellaris*).
Araneae:
  from the family Eutichuridae, *Cheiracanthium japonicum*, and the like;
  from the family Theridiidae, red-back spider (*Latrodectus hasseltii*), and the like.
Polydesmida:
  from the family Paradoxosomatidae, flat-backed millipede (*Oxidus gracilis*), *Nedyopus tambanus*, and the like;
Isopoda:
  from the family Armadillidiidae, common pill bug (*Armadillidium vulgare*), and the like;
Chilopoda:
  from the family Scutigeridae, *Thereuonema hilgendorfi*, and the like;
  from the family Scolopendridae, giant tropical centipede (*Scolopendra subspinipes*), and the like;
  from the family Ethopolyidae, *Bothropolys rugosus*, and the like;
Gastropoda:
  from the family Limacidae, tree slug (*Limax marginatus*), garden tawny slug (*Limax flavus*), and the like;
  from the family Philomycidae, *Meghimatium bilineatum*, and the like;
  from the family Ampullariidae, golden apple snail (*Pomacea canaliculata*), and the like;

from the family Lymnaeidae, *Austropeplea ollula*, and the like.

Nematoda:

from the family Aphelenchoididae, rice white-tip nematode (*Aphelenchoides besseyi*), and the like;

from the family Pratylenchidae, root lesion nematode (*Pratylenchus coffeae*), *Pratylenchus brachyurus*, California meadow nematode (*Pratylenchus neglectus*), *Radopholus similis*, and the like;

from the family Heteroderidae, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), white potato cyst nematode (*Globodera pallida*), and the like;

from the family Hoplolaimidae, *Rotylenchulus reniformis*, and the like;

from the family Anguinidae, strawberry bud nematode (*Nothotylenchus acris*), stem nematode (*Ditylenchus dipsaci*), and the like;

from the family Tylenchulidae, citrus nematode (*Tylenchulus semipenetrans*), and the like;

from the family Longidoridae, dagger nematode (*Xiphinema index*), and the like;

from the family Trichodoridae;

from the family Parasitaphelenchidae, pine wilt disease (*Bursaphelenchus xylophilus*), and the like.

The present compound may be also applied to harmful arthropods such as harmful insects and harmful mites, harmful mollusks, and harmful nematodes which have a reduced agent-sensitivity to or a developed agent-resistance to an insecticide or a miticide, a molluscicide or a nematicide.

The present compound may be also used to protect a plant from a plant disease caused by insect-borne viruses or insect-borne bacteria.

Examples of the insect-borne viruses are recited below.

Rice tungro spherical virus, Rice tungro bacilliform virus, Rice grassy stunt virus, Rice ragged stunt virus, Rice stripe virus, Rice black streaked dwarf virus, Southern rice blackstreaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, Chrysanthemum stem necrosis virus, Impatiens necrotic spot virus, Iris yellow spot virus, Lily mottle virus, Lilly symptomless virus, Tulip mosaic virus, and the others.

Examples of the insect-borne bacteria are recited below.

Candidatus *Phytoplasma oryzae*, Candidatus *Phytoplasma asteris*, Maize bushy stunt phytoplasma, Candidatus *Liberbacter asiaticus*, Candidatus *Liberbacter africanus*, Candidatus *Liberbacter americanus*.

The composition for controlling harmful arthropods of the present invention comprises the compound of the present invention and an inert active carrier. The composition for controlling harmful arthropods of the present invention is usually prepared by mixing the compound of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, water dispersible powders, flowables, dry flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. The composition for controlling harmful arthropods of the present invention comprises usually 0.0001 to 99.9% by weight of the compound of the present invention.

Examples of the solid carrier to be used in the formulation include fine powders or granules of clays (for example, kaolin clay, diatomaceous earth, bentonite, Fubasami clay, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF or dimethylacetamide); sulfoxides (for example, DMSO); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture with a usually kneader, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal, and so on). Also, the compound of the present invention can be applied to seeds. In the method for controlling harmful arthropods of the present invention, the Present compound is used usually in the form of a harmful arthropod controlling composition.

When a composition for controlling harmful arthropods of the present invention is used for controlling harmful arthropods in an agricultural field, the application dose as an amount of the compound of the present invention is usually within a range from 1 to 10,000 g per 10,000 m$^2$. When a composition for controlling harmful arthropods of the present invention is used for a seed treatment, an amount of the compound of the present invention is usually within a range from 0.001 to 100 g per 1 Kg of seeds. When a composition for controlling harmful arthropods of the present invention is formulated into an emulsifiable concentrate, a wettable powder, or a flowable formulation etc., the composition is usually applied by diluting it with water in such a way that a concentration of the compound of the present invention is within a range from 0.01 to 10,000 μm. The granular formulation, or the dust formulation etc., is usually applied as itself without diluting it.

These formulations or an aqueous dilution thereof can be spared directly to harmful arthropods or plants (such as crops) to be protected from harmful arthropods, and also may be applied to the soil of crop land in order to control harmful arthropods which live there.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control harmful arthropods that live inside a house, the application dose as an amount of the present compound is usually within a range from 0.01 to 1,000 mg per 1 m$^2$ of an area to be treated, in the case of using it on a planar area. In the case of using it spatially, the application dose as an amount of the present compound is usually within a range from 0.01 to 500 mg per 1 m$^3$ of the space to be treated. When the composition for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the composition for controlling harmful arthropods of the present invention is used for controlling external parasites of livestock such as cows, horses, pigs, sheep, goats and chickens and small animals such as dogs, cats, rats and mice, the composition of the present invention can be applied to the animals by a known method in the veterinary field. Specifically, when systemic control is intended, the control composition of the present invention is administered to the animals as a tablet, a mixture with feed or a suppository, or by injection (including intramuscular, subcutaneous, intravenous and intraperitoneal injections). On the other hand, when non-systemic control is intended, the composition of the present invention is applied to the animals by means of spraying of the oil solution or aqueous solution, pour-on or spot-on treatment, or washing the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

Further, the present compound can be used as an agent for controlling harmful arthropods in the agricultural land such as field, paddy, lawn and orchard. The compound of the present invention can control harmful arthropods in the agricultural land and so on, wherein the below-mentioned plants and so on are cultivated in the agricultural land.

Crops:

corn, rice, wheat, barley, rye, oat, sorghum, cotton, soybean, peanut, buckwheat, beet, rapeseed, sunflower, sugarcane, tobacco, and the others;

Vegetables:

solanaceous vegetables (for example, eggplant, tomato, green pepper, hot pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, dioscorea japonica, colocasia, flowering plants, foliage plants, and the others;

Fruits:

pomaceous fruits (for example, apple, pear, Japanese pear, Chinese quince, and quince), stone fleshy fruits (for example, peach, plum, nectarine, Prunus mume, cherry fruit, apricot, and prune), citrus fruits (for example, citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the others;

Trees Other than Fruits tea, mulberry, flowering plants, roadside trees (for example, ash, birch, dogwood, eucalyptus, Ginkgo biloba, lilac, maple, Quercus, poplar, Judas tree, Liquidambar formosana, plane tree, zelkova, Japanese arborvitae, fir wood, hemlock, juniper, Pinus, Picea, and Taxus cuspidate), The above-mentioned plants may be genetically modified crops.

EXAMPLES

Hereinafter, the present invention is explained in more detail by using Preparation example, Formulation example, and Test example, however, the present invention should not be limited to these examples.

As used herein, "Me" represents a methyl group, "Et" represents an ethyl group, and "Tf" represents a trifluoromethansulfonyl group.

Reference Preparation Example 1

A mixture of methyl (2-iodophenyl)acetate 0.95 g, (E)-2-cyclopropyl vinyl boronic acid 1 g, tetrakis(triphenylphosphine)palladium (0) 0.12 g, tripotassium phosphate 2.2 g, 1,4-dioxane 15 mL and water 3 mL was stirred at 100° C. for 8 hours. To the resulting mixture was added saturated aqueous ammonium chloride solution, and the mixture was extracted with MTBE. The resulting organic layer was dried over anhydrous magnesium sulfate, filtered, and concentrated under reduced pressure. The resulting residue was subjected to a silica gel column chromatography to an intermediate compound 1 represented by the below-mentioned formula 0.7 g.

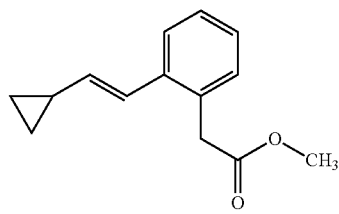 [SMILES: COC(=O)Cc1ccccc1/C=C/C1CC1]

Intermediate compound 1: $^1$H-NMR (CDCl$_3$) δ: 0.50 (2H, m), 0.83 (2H, m), 1.60 (1H, m), 3.69 (3H, s), 3.70 (2H, s), 5.60 (1H, dd), 6.66 (1H, d), 7.02-7.22 (3H, m), 7.39 (1H, d).

Reference Preparation Example 2

The compound which was prepared according to a similar method to that described in the Reference preparation example 1, and its physical properties are shown below.

A compound represented by formula (A-1):

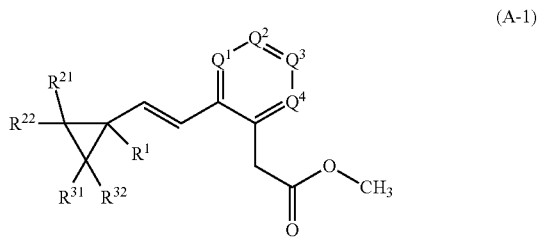

(A-1)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 1].

TABLE 1

| Intermediate compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 2 | H | H | H | H | H | CH | CF | CH | CH |
| 3 | H | H | H | H | H | CH | CCl | CH | CH |
| 4 | H | H | H | H | H | CH | CH | CCl | CH |
| 5 | H | H | H | H | H | CH | COMe | CH | CH |
| 6 | H | H | H | H | H | CH | N | CH | CH |
| 7 | H | H | H | H | H | CH | CH | CH | N |

Intermediate compound 2: $^1$H-NMR (CDCl$_3$) δ: 0.53 (2H, m), 0.85 (2H, m), 1.60 (1H, s), 3.66 (2H, s), 3.70 (3H, s), 5.60 (1H, dd), 6.59 (1H, d), 6.86 (1H, m), 7.07-7.15 (2H, m).

Intermediate compound 3: $^1$H-NMR (CDCl$_3$) δ: 0.52 (2H, m), 0.85 (2H, m), 1.58 (1H, m), 3.65 (2H, s), 3.70 (3H, s), 5.60 (1H, dd), 6.57 (1H, d), 7.11 (2H, s), 7.37 (1H, s).

Intermediate compound 4: $^1$H-NMR (CDCl$_3$) δ: 0.51 (2H, m), 0.85 (2H, m), 1.58 (1H, m), 3.66 (2H, s), 3.70 (3H, s), 5.58 (1H, dd), 6.57 (1H, d), 7.16-7.18 (2H, m), 7.31 (1H, d).

Intermediate compound 5: $^1$H-NMR (CDCl$_3$) δ: 0.51 (2H, m), 0.83 (2H, m), 1.59 (1H, m), 3.64 (2H, s), 3.69 (3H, s), 3.80 (3H, s), 5.59 (1H, dd), 6.62 (1H, d), 6.73 (1H, d), 6.92 (1H, s), 7.10 (1H, d).

Intermediate compound 6: $^1$H-NMR (CDCl$_3$) δ: 0.55 (2H, m), 0.87 (2H, m), 1.63 (1H, m), 3.68 (2H, s), 3.72 (3H, s), 5.66 (1H, dd), 6.56 (1H, d), 7.11 (1H, d), 8.37 (1H, d), 8.58 (1H, s).

Reference Preparation Example 3

To a mixture of 2-bromo-4-(trifluoromethyl)phenol 2 g, pyridinium p-toluene sulfonate 0.21 g, and chloroform 28 mL was added 3,4-dihydro-2H-pyran 1.4 g, and the mixture was stirred at room temperature for 8 hours. To the resulting mixture was added saturated aqueous sodium hydrogen carbonate solution, and the mixture was extracted with chloroform. The resulting organic layer was dried over anhydrous magnesium sulfate, filtered, and concentrated under reduced pressure. The resulting residue was subjected to a silica gel column chromatography to obtain the intermediate compound 8 represented by the following formula 3 g.

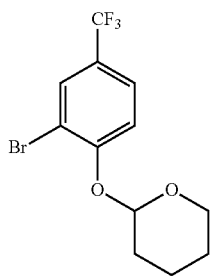 [SMILES: FC(F)(F)c1ccc(OC2CCCCO2)c(Br)c1]

Intermediate compound 8: $^1$H-NMR (CDCl$_3$) δ: 1.6-2.2 (6H, m), 3.60 (1H, m), 3.81 (1H, m), 5.60 (1H m), 7.22 (1H, d), 7.50 (1H, d), 7.80 (1H, s).

Reference Preparation Example 4

The intermediate compound 9 represented by the below-mentioned formula was obtained by using the intermediate compound 8 in place of (2-iodophenyl)acetate according to a similar method to that described in the Reference preparation example 1.

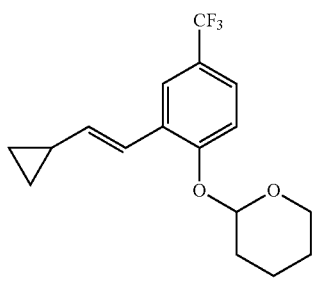 [SMILES: FC(F)(F)c1ccc(OC2CCCCO2)c(/C=C/C2CC2)c1]

Intermediate compound 9: $^1$H-NMR (CDCl$_3$) δ: 0.55 (2H, m), 0.87 (2H, m), 1.6-2.2 (7H, m), 3.75 (1H, m), 3.83 (1H, m), 5.51 (1H, m), 5.80 (1H, dd), 6.80 (1H, d), 7.16 (1H, d), 7.35 (1H, d), 7.60 (1H, s).

Reference Preparation Example 5

To a mixture of the intermediate compound 9 2.8 g and methanol 30 mL was added concentrated hydrochloric acid 0.05 g, and the mixture was stirred at room temperature for 4 hours. To the resulting mixture was added saturated aqueous sodium hydrogen carbonate solution, and the mixture was extracted with chloroform. The resulting organic layer was dried over anhydrous magnesium sulfate, filtered, and concentrated under reduced pressure. The resulting residue was subjected to a silica gel column chromatography to obtain the intermediate compound 10 represented by the below-mentioned formula.

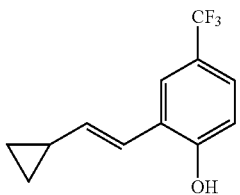 [SMILES: Oc1ccc(C(F)(F)F)cc1/C=C/C1CC1]

Intermediate Compound 10

To a mixture of the obtained intermediate compound 10, chloroform 32 mL, and pyridine 2.3 g was added trifluoromethansulfonyl anhydride 4.1 g at 0° C., and the mixture was stirred for 8 hours. To the resulting mixture was added saturated aqueous sodium ammonium chloride solution, and the mixture was extracted with MTBE. The resulting organic layer was dried over anhydrous magnesium sulfate, filtered, and concentrated under reduced pressure. The resulting residue was subjected to a silica gel column chromatography to obtain the intermediate compound 11 represented by the below-mentioned formula 2.7 g.

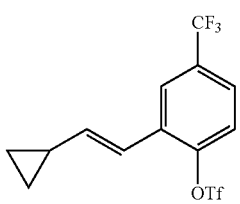 [SMILES: O=S(=O)(Oc1ccc(C(F)(F)F)cc1/C=C/C1CC1)C(F)(F)F]

Intermediate compound 11: $^1$H-NMR (CDCl$_3$) δ: 0.57 (2H, m), 0.87 (2H, m), 1.61 (1H, m), 5.80 (1H, dd), 7.26 (1H, d), 7.38 (1H, d), 7.70 (1H, s), 7.83 (1H, d).

Reference Preparation Example 6

The intermediate compound 12 represented by the below-mentioned formula 0.63 g was obtained by using 2-bromo-1-{[tert-butyl]dimethylsilyl]oxy}-4-methylbenzene in place of (2-iodophenyl)acetate according to a similar method to that described in the Reference Preparation Example 1.

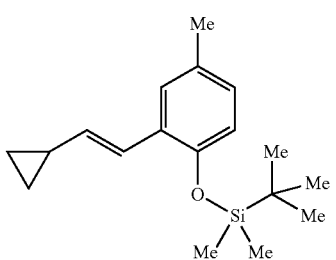 [SMILES: Cc1ccc(O[Si](C)(C)C(C)(C)C)c(/C=C/C2CC2)c1]

Intermediate compound 12: $^1$H-NMR (CDCl$_3$) δ: 0.19 (6H, s), 0.49 (2H, m), 0.79 (2H, m), 1.02 (9H, s), 1.55 (1H, s), 2.25 (3H, s), 5.69 (1H, dd), 6.47 (1H, d), 6.72 (1H, d), 6.85 (1H, d), 7.17 (1H, s).

Reference Preparation Example 7

The compounds which were prepared according to a similar method to that described in the Reference preparation example 6, and their physical properties are shown below.

A compound represented by formula (A-2):

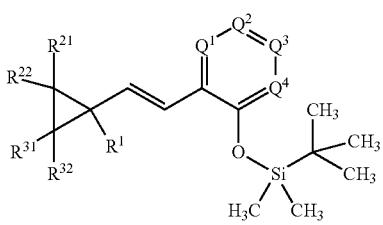

(A-2)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 2].

TABLE 2

| Intermediate compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 13 | H | H | H | H | H | CH | CH | CMe | CH |
| 14 | H | H | H | H | H | CH | CH | CH | CMe |

Intermediate compound 13: $^1$H-NMR (CDCl$_3$) δ: 0.10 (6H, s), 0.49 (2H, m), 0.81 (2H, m), 1.59 (1H, m), 2.05 (9H, s), 2.27 (3H, s), 5.65 (1H, dd), 6.58-6.69 (3H, m), 7.14 (1H, d).

Intermediate compound 14: $^1$H-NMR (CDCl$_3$) δ: 0.16 (6H, s), 0.48 (2H, m), 0.78 (2H, m), 1.06 (9H, s), 1.52 (1H, m)), 2.20 (3H, s), 5.58 (1H, dd), 6.68 (1H, d), 6.81 (1H, m), 6.96 (1H, m), 7.20 (1H, m).

Reference Preparation Example 8

The intermediate compound 15 represented by the below-mentioned formula was obtained by using 2-bromo-1-{[(tert-butyl)dimethylsilyl]oxy}-3-chlorobenzene in place of methyl (2-iodophenyl)acetate according to a similar method to that described in the Reference preparation example 1.

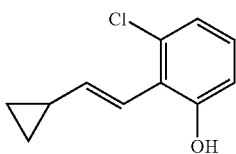 [SMILES: Oc1cccc(Cl)c1/C=C/C1CC1]

Intermediate compound 15: $^1$H-NMR (CDCl$_3$) δ: 0.45 (2H, m), 0.79 (2H, m), 1.51 (1H, m), 5.47 (1H, s), 5.54 (1H, dd), 6.35 (1H, d), 6.70 (1H, d), 6.83 (1H, d), 6.92 (1H, t).

Reference Preparation Example 9

The compounds which were prepared according to a similar method to that described in the Reference preparation example 8, and their physical properties are shown below.

A compound represented by formula (A-3):

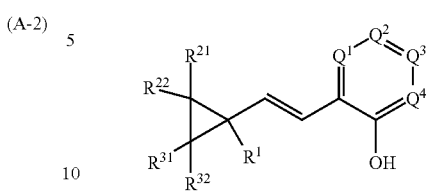

(A-3)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 3].

TABLE 3

| Intermediate compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 16 | H | H | H | H | H | CH | CEt | CH | CH |
| 17 | H | H | H | H | H | N | CH | CH | CH |

Intermediate compound 16: $^1$H-NMR (CDCl$_3$) δ: 0.52 (2H, m), 0.83 (2H, m), 1.20 (3H, t), 1.60 (1H, m), 2.55 (2H, q), 4.76 (1H, s), 5.69 (1H, dd), 6.42 (1H, d), 6.70 (1H, d), 6.90 (1H, d), 7.09 (1H, s).

Intermediate compound 17: $^1$H-NMR (CDCl$_3$) δ: 0.57 (2H, m), 0.84 (2H, m), 1.63 (1H, m), 2.05 (1H, s), 6.33 (1H, dd), 6.88 (1H, d), 6.99 (1H, t), 7.08 (1H, d), 8.08 (1H, d).

Reference Preparation Example 10

To a mixture of the intermediate compound 12 0.63 g, tetrahydrofuran 11 mL and acetic acid 0.7 mL was added tetrabutyl ammonium fluoride (1M tetrahydrofuran solution) 2.6 mL, and the mixture was stirred for 1 hour. To the resulting mixture was added saturated aqueous ammonium chloride solution, and the mixture was extracted with MTBE. The resulting organic layer was dried over anhydrous magnesium sulfate, filtered, and concentrated under reduced pressure. The resulting residues were subjected to a silica gel column chromatography to obtain the intermediate compound 18 represented by the below-mentioned formula 0.5 g.

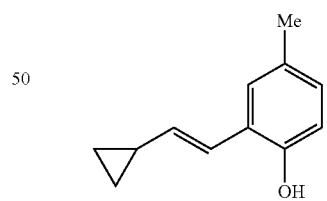

Intermediate compound 18: $^1$H-NMR (CDCl$_3$) δ: 0.51 (2H, m), 0.82 (2H, m), 1.59 (1H, m), 2.25 (3H, s), 4.77 (1H, s), 5.68 (1H, dd), 6.62 (1H, d), 6.67 (1H, d), 6.87 (1H, d), 7.08 (1H, s).

Reference Preparation Example 11

The compounds which were prepared according to a similar method to that described in the Reference preparation example 10, and their physical properties are shown below.

A compound represented by formula (A-3):

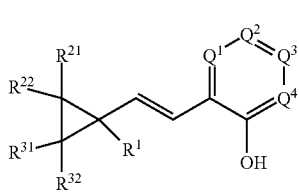

(A-3)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 4].

TABLE 4

| Intermediate compound | $R^1$ | $R^{21}$ | $R^{22}$ | $R^{31}$ | $R^{32}$ | $Q^1$ | $Q^2$ | $Q^3$ | $Q^4$ |
| --- | --- | --- | --- | --- | --- | --- | --- | --- | --- |
| 19 | H | H | H | H | H | CH | CH | CMe | CH |
| 20 | H | H | H | H | H | CH | CH | CH | CMe |

Intermediate compound 19: $^1$H-NMR (CDCl$_3$) δ: 0.50 (2H, m), 0.81 (2H, m), 1.57 (1H, m), 2.27 (3H, s), 4.88 (1H, s), 5.65 (1H, dd), 6.58-6.69 (3H, m), 7.14 (1H, d).

Intermediate compound 20: $^1$H-NMR (CDCl$_3$) δ: 0.51 (2H, m), 0.83 (2H, m), 1.60 (1H, m), 2.24 (3H, s), 4.91 (1H, s), 5.66 (1H, dd), 6.43 (1H, d), 6.78 (1H, m), 6.98 (1H, d), 7.10 (1H, d).

Reference Preparation Example 12

To a mixture of the intermediate compound 18 0.5 g, chloroform 14 mL, and pyridine 0.45 g was added trifluoromethansulfonic anhydride 0.98 g at 0° C., and the mixture was stirred for 8 hours. To the resulting mixture was added saturated aqueous ammonium chloride solution, and the mixture was extracted with MTBE. The resulting organic layer was dried over anhydrous magnesium sulfate, filtered, and concentrated under reduced pressure. The resulting residue was subjected to a silica gel column chromatography to obtain the intermediate compound 21 represented by the below-mentioned formula 0.5 g.

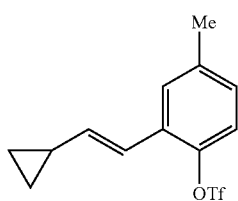 [SMILES: Cc1ccc(OS(=O)(=O)C(F)(F)F)c(/C=C/C2CC2)c1]

Intermediate compound 21: $^1$H-NMR (CDCl$_3$) δ: 0.56 (2H, m), 0.87 (2H, m), 1.62 (1H, m), 2.34 (3H, s), 5.80 (1H, dd), 6.59 (1H, d), 7.03 (1H, d), 7.10 (1H, d), 7.31 (1H, s).

Reference Preparation Example 13

The compound prepared according to a similar method to that described in the Reference preparation example 12 and its physical properties are shown below.

A compound represented by formula (A-4):

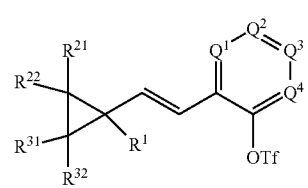

(A-4)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 5].

TABLE 5

| Intermediate compound | $R^1$ | $R^{21}$ | $R^{22}$ | $R^{31}$ | $R^{32}$ | $Q^1$ | $Q^2$ | $Q^3$ | $Q^4$ |
| --- | --- | --- | --- | --- | --- | --- | --- | --- | --- |
| 22 | H | H | H | H | H | CH | CH | CMe | CH |
| 23 | H | H | H | H | H | CH | CH | CH | CMe |
| 24 | H | H | H | H | H | CCl | CH | CH | CH |
| 25 | H | H | H | H | H | CH | CEt | CH | CH |
| 26 | H | H | H | H | H | N | CH | CH | CH |

Intermediate compound 22: $^1$H-NMR (CDCl$_3$) δ: 0.54 (2H, m), 0.87 (2H, m), 1.61 (1H, m), 2.35 (3H, s), 5.77 (1H, dd), 6.58 (1H, d), 7.02 (1H, s), 7.09 (1H, d), 7.39 (1H, d).

Intermediate compound 23: $^1$H-NMR (CDCl$_3$) δ: 0.55 (2H, m), 0.86 (2H, m), 1.61 (1H, m), 2.38 (3H, s), 5.78 (1H, dd), 6.64 (1H, d), 7.09-7.19 (2H, m), 7.34 (1H, m).

Intermediate compound 24: $^1$H-NMR (CDCl$_3$) δ: 0.59 (2H, m), 0.88 (2H, m), 1.65 (1H, m), 5.78 (1H, dd), 6.42 (1H, d), 7.17 (2H, d), 7.40 (1H, t).

Intermediate compound 25: $^1$H-NMR (CDCl$_3$) δ: 0.57 (2H, m), 0.87 (2H, m), 1.24 (3H, t), 1.62 (1H, m), 2.63 (2H, q), 5.81 (1H, dd), 6.60 (1H, d), 7.05 (1H, d), 7.12 (1H, d), 7.32 (1H, s).

Intermediate compound 26: $^1$H-NMR (CDCl$_3$) δ: 0.68 (2H, m), 0.95 (2H, m), 1.71 (1H, m), 6.60 (1H, dd), 6.78 (1H, d), 7.17 (1H, t), 7.55 (1H, d), 8.49 (1H, d).

Reference Preparation Example 14

To a mixture of 2-hydroxy-5-methoxybenzaldehyde 10 g, pyridine 8.5 mL and chloroform 160 mL was added trifluoromethansulfonyl anhydride 14 mL at 0° C., and the mixture was stirred at room temperature for 25 hours. The resulting mixture was cooled to 0° C., and thereto was added 1N hydrochloric acid, and the mixture was extracted with chloroform. The resulting organic layer was washed with saturated aqueous sodium hydrogen carbonate solution and saturated brine successively, dried over anhydrous sodium sulfate, filtered, and concentrated under reduced pressure. The resulting residue was subjected to a silica gel column chromatography to obtain the intermediate compound 27 represented by the below-mentioned formula 15 g.

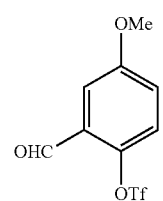 [SMILES: COc1ccc(OS(=O)(=O)C(F)(F)F)c(C=O)c1]

Intermediate compound 27: $^1$H-NMR (CDCl$_3$) δ: 3.89 (3H, s), 7.21 (1H, dd), 7.33 (1H, d), 7.44 (1H, d), 10.24 (1H, s).

Reference Preparation Example 15

The compound prepared according to a similar method to that described in the Reference preparation example 14 and its physical properties are shown below.

A compound represented by formula (A-5):

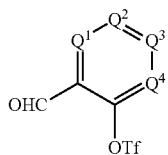

(A-5)

wherein a combination of $Q^1$, $Q^2$, $Q^3$ and $Q^4$ represents any combinations indicated in [Table 6].

TABLE 6

| Intermediate compound | $Q^1$ | $Q^2$ | $Q^3$ | $Q^4$ |
|---|---|---|---|---|
| 28 | CH | CF | CH | CH |

Intermediate compound 28: $^1$H-NMR (CDCl$_3$) δ: 7.46-7.39 (2H, m), 7.69 (1H, m), 10.24 (1H, d).

Reference Preparation Example 16

To a mixture of the intermediate compound 27 15 g and methanol 180 mL was added sodium borohydride 3.0 g at 0° C., and the mixture was stirred at room temperature for 20 minutes. The resulting mixture was concentrated under reduced pressure, and water was added to the residue, and the mixture was extracted with ethyl acetate. The resulting organic layer was washed with water and saturated brine successively, dried over anhydrous sodium sulfate, filtered, and concentrated under reduced pressure. The resulting residue was subjected to a silica gel column chromatography to obtain the intermediate compound 29 represented by the below-mentioned formula 13 g.

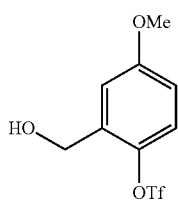 [SMILES: COc1ccc(OS(=O)(=O)C(F)(F)F)c(CO)c1]

Intermediate compound 29: $^1$H-NMR (CDCl$_3$) δ: 3.84 (3H, s), 4.77 (1H, s), 4.78 (1H, s), 6.86 (1H, dd), 7.12 (1H, d), 7.18 (1H, d).

Reference Preparation Example 17

The compounds which were prepared according to a similar method to that described in the Reference preparation example 16, and their physical properties are shown below.

A compound represented by formula (A-6):

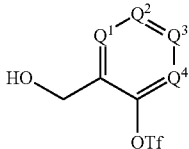

(A-6)

wherein a combination of $Q^1$, $Q^2$, $Q^3$ and $Q^4$ represents any combinations indicated in [Table 7].

TABLE 7

| Intermediate compound | $Q^1$ | $Q^2$ | $Q^3$ | $Q^4$ |
|---|---|---|---|---|
| 30 | CH | CF | CH | CH |
| 31 | CH | CMe | CH | CH |

Intermediate compound 30: $^1$H-NMR (CDCl$_3$) δ: 4.79 (1H, s), 4.81 (1H, s), 7.06 (1H, m), 7.25 (1H, dd), 7.37 (1H, dd).

Intermediate compound 31: $^1$H-NMR (CDCl$_3$) δ: 2.38 (3H, s), 4.74 (1H, s), 4.76 (1H, s), 7.13-7.18 (2H, m), 7.40 (1H, m).

Reference Preparation Example 18

To a mixture of the intermediate compound 29 13 g and diethyl ether 154 mL was added tribromide phosphate 6.5 mL at 0° C., and the mixture was stirred at room temperature for 15 hours. The resulting mixture was cooled to 0° C., and water was added thereto, and the mixture was extracted with MTBE. The resulting organic layer was washed with water and saturated brine successively, and the mixture was dried over anhydrous magnesium sulfate, filtered, and concentrated under reduced pressure. To the resulting residue were added toluene 18 mL and trimethyl phosphite 5.5 mL, and the mixture was stirred under reflux for 96 hours. The resulting mixture was cooled to room temperature, and thereto was then added ethyl acetate, and the mixture was washed with saturated aqueous ammonium chloride solution and saturated brine successively. The resulting organic layer was dried over anhydrous sodium sulfate, filtered, and concentrated under reduced pressure. The resulting residue was subjected to a silica gel column chromatography to obtain the intermediate compound 32 represented by the below-mentioned formula 1.8 g.

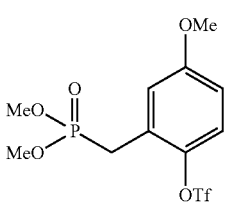 [SMILES: COc1ccc(OS(=O)(=O)C(F)(F)F)c(CP(=O)(OC)OC)c1]

Intermediate compound 32: $^1$H-NMR (CDCl$_3$) δ: 3.20 (1H, s), 3.26 (1H, s), 3.71 (3H, s), 3.74 (3H, s), 3.82 (3H, s), 6.84 (1H, m), 7.05 (1H, m), 7.21 (1H, m).

Reference Preparation Example 19

The compounds which were prepared according to a similar method to that described in the Reference preparation example 18, and their physical properties are shown below.

A compound represented by formula (A-7):

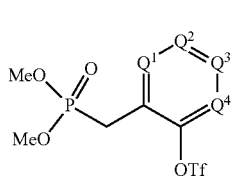

wherein a combination of $Q^1$, $Q^2$, $Q^3$ and $Q^4$ represents any combinations indicated in [Table 8].

TABLE 8

| Intermediate compound | $Q^1$ | $Q^2$ | $Q^3$ | $Q^4$ |
|---|---|---|---|---|
| 33 | CH | CF | CH | CH |
| 34 | CH | CCl | CH | CH |
| 35 | CH | CMe | CH | CH |

Intermediate compound 33: $^1$H-NMR (CDCl$_3$) δ: 3.22 (1H, s), 3.27 (1H, s), 3.73 (3H, s), 3.76 (3H, s), 7.06 (1H, m), 7.26-7.31 (2H, m).

Intermediate compound 34: $^1$H-NMR (CDCl$_3$) δ: 3.20 (1H, s), 3.26 (1H, s), 3.73 (3H, s), 3.76 (3H, s), 7.25 (1H, d), 7.33 (1H, m), 7.53 (1H, m).

Intermediate compound 35: $^1$H-NMR (CDCl$_3$) δ: 2.37 (3H, s), 3.20 (1H, s), 3.25 (1H, s), 3.71 (3H, s), 3.73 (3H, s), 7.14 (1H, d), 7.18 (1H, d), 7.33 (1H, s).

Reference Preparation Example 20

To a mixture of 2,2-difluorocyclopropane carboxylic acid 1.7 g and chloroform 40 mL were added N,O-dimethylhydroxylamine hydrochloride salts 1.8 g, 4-methyl morpholine 2.1 mL, N,N'-diisopropyl carbodiimide 3.3 g, and 1-hydroxybenzotriazole 0.2 g successively, and the mixture was stirred at room temperature for 13 hours. To the resulting mixture was added chloroform, and the mixture was washed with 1M hydrochloric acid, saturated aqueous sodium hydrogen carbonate solution, and saturated brine successively, dried over anhydrous sodium sulfate, filtered, and concentrated under reduced pressure. The resulting residue was subjected to a silica gel column chromatography to obtain the intermediate compound 36 represented by the below-mentioned formula 2.1 g.

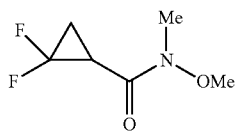 [SMILES: CON(C)C(=O)C1CC1(F)F]

Intermediate compound 36: $^1$H-NMR (CDCl$_3$) δ: 1.69 (1H, m), 2.16 (1H, m), 2.94 (1H, m), 3.26 (3H, s), 3.77 (3H, s).

Reference Preparation Example 21

The compounds which were prepared according to a similar method to that described in the Reference preparation example 20, and their physical properties are shown below.

A compound represented by formula (A-8):

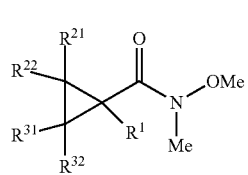

wherein a combination of $Q^1$, $Q^2$, $Q^3$ and $Q^4$ represents any combinations indicated in Table 9.

TABLE 9

| Intermediate compound | $R^1$ | $R^{21}$ | $R^{22}$ | $R^{31}$ | $R^{32}$ |
|---|---|---|---|---|---|
| 37 | H | Me | Me | H | H |
| 38 | Me | H | H | H | H |
| 39 | H | Me | H | H | H |
| 40 | H | Me | Me | Me | Me |

Intermediate compound 37: $^1$H-NMR (CDCl$_3$) δ: 0.77 (1H, dd), 1.13 (3H, s), 1.18 (1H, t), 1.20 (3H, s), 1.95 (1H, m), 3.22 (3H, s), 3.71 (3H, s).

Intermediate compound 38: $^1$H-NMR (CDCl$_3$) δ: 0.55-0.57 (2H, m), 1.03-1.05 (2H, m), 1.37 (3H, s), 3.23 (3H, s), 3.77 (3H, s).

Intermediate compound 39: $^1$H-NMR (CDCl$_3$) δ: 0.65 (1H, m), 1.13 (3H, d), 1.18 (1H, m), 1.36 (1H, m), 1.85 (1H, m), 3.20 (3H, s), 3.75 (3H, s).

Intermediate compound 40: $^1$H-NMR (CDCl$_3$) δ: 1.20 (6H, s), 1.26 (6H, s), 1.57 (1H, s), 3.17 (3H, s), 3.67 (3H, s).

Reference Preparation Example 22

To a mixture of the intermediate compound 36 2.0 g and toluene 16 mL was added diisobutylaluminium hydride (1M toluene solution) at −78° C., and the mixture was stirred for 4 hours. To the resulting mixture was added ethyl acetate 2.4 mL, and the mixture was stirred at room temperature for 30 minutes. The resulting mixture was cooled to 0° C., and thereto was added aqueous sodium potassium tartrate solution 40 mL, and the mixture was stirred at room temperature for 16 hours. The resulting mixture was separated into the organic layer and the aqueous layer.

To the resulting organic layer were added dimethyl=[(2-iodophenyl)methyl]phosphonate 2.6 g and lithium chloride 0.41 g successively, and the mixture was stirred at 0° C. To the resulting mixture was added sodium hydride (60%, oily) 0.39 g, and the mixture was stirred at room temperature for 16 hours. Water was added to the resulting mixture, and the mixture was extracted with ethyl acetate. The resulting organic layer was washed with saturated aqueous ammonium chloride solution and saturated brine successively, dried over anhydrous sodium sulfate, filtered, and concentrated under reduced pressure. The resulting residue was subjected to a silica gel column chromatography to obtain the intermediate compound 41 represented by the below-mentioned formula 1.2 g.

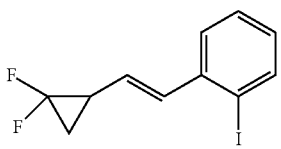 [SMILES: FC1(F)CC1/C=C/c1ccccc1I]

Intermediate compound 41: $^1$H-NMR (CDCl$_3$) δ: 1.92-1.94 (3H, m), 6.11 (1H, m), 6.58 (1H, d), 6.89 (1H, td), 7.27 (1H, t), 7.43 (1H, dd), 7.81 (1H, d).

Reference Preparation Example 23

The compounds which were prepared according to a similar method to that described in the Reference preparation example 22, and their physical properties are shown below.

A compound represented by formula (A-9):

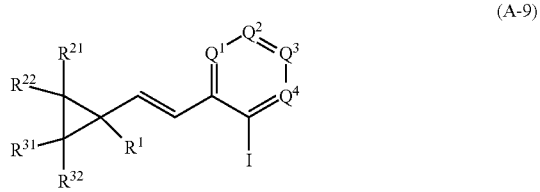

(A-9)

wherein a combination of R$^1$, R$^{21}$, R$^{22}$, R$^{31}$, R$^{32}$, Q$^1$, Q$^2$, Q$^3$, and Q$^4$ represents any combinations indicated in [Table 10].

TABLE 10

| Intermediate compound | R$^1$ | R$^{21}$ | R$^{22}$ | R$^{31}$ | R$^{32}$ | Q$^1$ | Q$^2$ | Q$^3$ | Q$^4$ |
|---|---|---|---|---|---|---|---|---|---|
| 42 | H | Me | Me | H | H | CH | CH | CH | CH |
| 43 | Me | H | H | H | H | CH | CH | CH | CH |
| 44 | H | Me | H | H | H | CH | CH | CH | CH |
| 45 | H | Me | Me | Me | Me | CH | CH | CH | CH |

Intermediate compound 42: $^1$H-NMR (CDCl$_3$) δ: 0.54 (1H, t), 0.82 (1H, dd), 1.15 (6H, s), 1.50 (1H, m), 5.87 (1H, dd), 6.63 (1H, d), 6.86 (1H, td), 7.25 (1H, td), 7.41 (1H, dd), 7.81 (1H, dd).

Intermediate compound 43: $^1$H-NMR (CDCl$_3$) δ: 0.70-0.75 (4H, m), 1.33 (3H, s), 5.68 (1H, d), 6.50 (1H, d), 6.86 (1H, td), 7.25 (1H, m), 7.38 (1H, dd), 7.81 (1H, dd).

Intermediate compound 44: $^1$H-NMR (CDCl$_3$) δ: 0.63 (1H, m), 0.72 (1H, m), 0.92 (1H, m), 1.13 (3H, d), 1.34 (1H, m), 5.64 (1H, dd), 6.59 (1H, d), 6.85 (1H, td), 7.24 (1H, t), 7.38 (1H, dd), 7.80 (1H, d).

Intermediate compound 45: $^1$H-NMR (CDCl$_3$) δ: 1.11 (6H, s), 1.18 (6H, s), 1.20 (1H, d), 5.93 (1H, dd), 6.63 (1H, d), 6.86 (1H, td), 7.25 (1H, t), 7.43 (1H, dd), 7.81 (1H, dd).

A compound represented by formula (A-10):

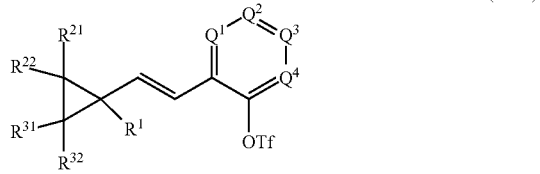

(A-10)

wherein a combination of R$^1$, R$^{21}$, R$^{22}$, R$^{31}$, R$^{32}$, Q$^1$, Q$^2$, Q$^3$, and Q$^4$ represents any combinations indicated in [Table 11].

TABLE 11

| Intermediate compound | R$^1$ | R$^{21}$ | R$^{22}$ | R$^{31}$ | R$^{32}$ | Q$^1$ | Q$^2$ | Q$^3$ | Q$^4$ |
|---|---|---|---|---|---|---|---|---|---|
| 46 | H | Me | Me | H | H | CH | CF | CH | CH |
| 47 | H | Me | Me | H | H | CH | CMe | CH | CH |
| 48 | H | Me | H | H | H | CH | CMe | CH | CH |
| 49 | H | Me | Me | H | H | CH | COMe | CH | CH |
| 50 | H | Me | Me | H | H | CH | CCl | CH | CH |

Intermediate compound 46: $^1$H-NMR (CDCl$_3$) δ: 0.59 (1H, t), 0.88 (1H, dd), 1.15 (6H, s), 1.49 (1H, m), 6.07 (1H, dd), 6.58 (1H, d), 6.92 (1H, m), 7.14-7.25 (2H, m).

Intermediate compound 47: $^1$H-NMR (CDCl$_3$) δ: 0.56 (1H, t), 0.84 (1H, dd), 1.15 (6H, s), 1.48 (1H, m), 2.35 (3H, s), 6.05 (1H, dd), 6.59 (1H, d), 7.02 (1H, dd), 7.10 (1H, d), 7.32 (1H, d).

Intermediate compound 48: $^1$H-NMR (CDCl$_3$) δ: 0.64 (1H, m), 0.74 (1H, m), 0.93 (1H, m), 1.13 (3H, d), 1.31 (1H, m), 2.33 (3H, s), 5.84 (1H, dd), 6.53 (1H, d), 7.01 (1H, dd), 7.09 (1H, d), 7.30 (1H, d).

Intermediate compound 49: $^1$H-NMR (CDCl$_3$) δ: 0.57 (1H, t), 0.85 (1H, dd), 1.14 (6H, s), 1.48 (1H, m), 3.82 (3H, s), 6.05 (1H, dd), 6.58 (1H, d), 6.74 (1H, dd), 6.99 (1H, d), 7.14 (1H, d).

Intermediate compound 50: $^1$H-NMR (CDCl$_3$) δ: 0.59 (1H, t), 0.88 (1H, dd), 1.15 (6H, s), 1.49 (1H, m), 6.08 (1H, dd), 6.55 (1H, d), 7.15-7.20 (2H, m), 7.50 (1H, d).

Reference Preparation Example 24

To a mixture of the intermediate compound 41 0.73 g and THF 10 mL were added copper(I) iodide 0.10 g, pinacolborane 0.52 mL and sodium hydride (60%, oily) 0.14 g successively, and the mixture was stirred for 55 hours. To the resulting mixture was added MTBE, and the mixture was washed with saturated aqueous ammonium chloride solution and saturated brine successively, dried over anhydrous magnesium sulfate, filtered, and concentrated under reduced pressure. The resulting residue was subjected to a silica gel column chromatography to obtain the intermediate compound 51 represented by the below-mentioned formula 0.47 g.

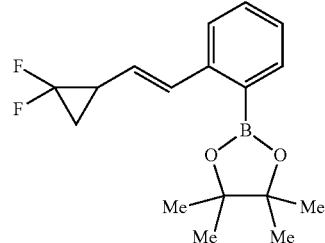 [SMILES: CC1(C)OB(c2ccccc2/C=C/C2CC2(F)F)OC1(C)C]

Intermediate compound 51: $^1$H-NMR (CDCl$_3$) δ: 1.36 (12H, s), 1.37 (1H, m), 1.69 (1H, m), 2.42 (1H, m), 5.86 (1H, m), 7.22 (1H, td), 7.37 (1H, td), 7.42 (1H, d), 7.53 (1H, d), 7.78 (1H, dd).

Reference Preparation Example 25

The compounds which were prepared according to a similar method to that described in the Reference preparation example 24, and their physical properties are shown below.

A compound represented by formula (A-11):

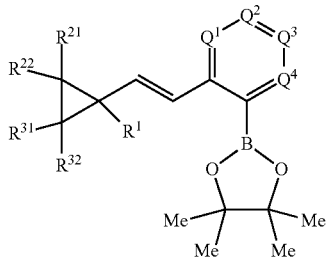

(A-11)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 12].

TABLE 12

| Intermediate compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 52 | H | Me | Me | H | H | CH | CH | CH | CH |
| 53 | Me | H | H | H | H | CH | CH | CH | CH |
| 54 | H | Me | H | H | H | CH | CH | CH | CH |
| 55 | H | Me | Me | Me | Me | CH | CH | CH | CH |

Intermediate compound 52: $^1$H-NMR (CDCl$_3$) δ: 0.53 (1H, dd), 0.75 (1H, dd), 1.13 (3H, s), 1.14 (3H, s), 1.36 (12H, s), 1.45 (1H, m), 5.99 (1H, dd), 7.15 (1H, td), 7.23 (1H, d), 7.33 (1H, td), 7.53 (1H, d), 7.74 (1H, dd).

Intermediate compound 53: 1H-NMR (CDCl$_3$) δ: 0.66-0.70 (4H, m), 1.31 (3H, s), 1.36 (12H, s), 5.76 (1H, d), 7.24 (2H, m), 7.33 (1H, td), 7.49 (1H, d), 7.73 (1H, dd).

Intermediate compound 54: $^1$H-NMR (CDCl$_3$) δ: 0.58 (1H, m), 0.70 (1H, m), 0.90 (1H, m), 1.13 (3H, d), 1.29 (1H, m), 1.36 (12H, s), 5.78 (1H, dd), 7.14 (1H, t), 7.20 (1H, d), 7.32 (1H, m), 7.48 (1H, d), 7.73 (1H, d).

Intermediate compound 55; $^1$H-NMR (CDCl$_3$) δ: 1.10 (6H, s), 1.13-1.17 (7H, m), 1.37 (12H, s), 6.03 (1H, dd), 7.14 (1H, t), 7.26 (1H, d), 7.33 (1H, t), 7.55 (1H, d), 7.74 (1H, d).

Reference Preparation Example 26

A mixture of the intermediate compound 49 0.53 g, potassium acetate 0.45 g, bis(pinacolato)diboron 0.50 g, [1,1'-bis(diphenylphoshino)ferrocene] palladium (II) dichloride dichloromethane adduct 0.07 g, and 1,4-dioxane 8 mL was stirred under reflux for 22 hours. The resulting mixture was cooled to room temperature, and water was then added thereto, and the mixture was extracted with MTBE. The resulting organic layer was washed with saturated brine, dried over anhydrous magnesium sulfate, filtered, and concentrated under reduced pressure. The resulting residue was subjected to a silica gel column chromatography to obtain the intermediate compound 56 represented by the following formula 0.25 g.

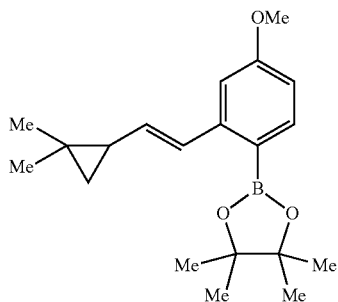 [SMILES: COc1ccc(B2OC(C)(C)C(C)(C)O2)c(/C=C/C2CC2(C)C)c1]

Intermediate compound 56: $^1$H-NMR (CDCl$_3$) δ: 0.53 (1H, t), 0.76 (1H, dd), 1.13 (3H, s), 1.15 (3H, s), 1.34 (12H, s), 1.45 (1H, m), 3.82 (3H, s), 5.99 (1H, dd), 6.72 (1H, dd), 7.04 (1H, d), 7.26 (1H, d), 7.71 (1H, d).

Reference Preparation Example 27

The compounds which were prepared according to a similar method to that described in the Reference preparation example 26, and their physical properties are shown below.

A compound represented by formula (A-11):

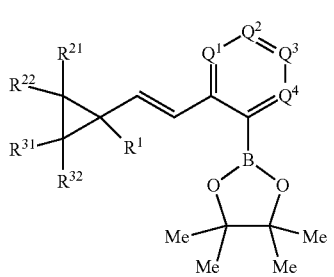

(A-11)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 13].

TABLE 13

| Intermediate compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 57 | H | H | H | H | H | CCl | CH | CH | CH |
| 58 | H | H | H | H | H | CH | CMe | CH | CH |
| 59 | H | H | H | H | H | CH | CEt | CH | CH |
| 60 | H | H | H | H | H | CH | CH | CMe | CH |
| 61 | H | H | H | H | H | CH | CH | CH | CMe |
| 62 | H | H | H | H | H | CH | CF$_3$ | CH | CH |
| 63 | H | Me | Me | H | H | CH | CMe | CH | CH |
| 64 | H | Me | H | H | H | CH | CMe | CH | CH |
| 65 | H | Me | Me | H | H | CH | CF | CH | CH |
| 66 | H | Me | Me | H | H | CH | CCl | CH | CH |

Intermediate compound 57: $^1$H-NMR (CDCl$_3$) δ: 0.54 (2H, m), 0.81 (2H, m), 1.34 (12H, s), 1.62 (1H, m), 5.46 (1H, dd), 6.82 (1H, d), 7.12 (1H, t), 7.37 (1H, d), 7.49 (1H, d).

Intermediate compound 58: $^1$H-NMR (CDCl$_3$) δ: 0.52 (2H, m), 0.80 (2H, m), 1.35 (12H, s), 1.59 (1H, m), 2.32 (3H, s), 5.73 (1H, dd), 6.98 (1H, d), 7.24-7.31 (2H, m), 7.65 (1H, d).

Intermediate compound 59: $^1$H-NMR (CDCl$_3$) δ: 0.53 (2H, m), 0.81 (2H, m), 1.22 (3H, t), 1.35 (12H, s), 1.62 (1H, m), 2.61 (2H, q), 5.74 (1H, dd), 7.01 (1H, d), 7.28 (1H, d), 7.33 (1H, s), 7.68 (1H, d).

Intermediate compound 60: $^1$H-NMR (CDCl$_3$) δ: 0.50 (2H, m), 0.80 (2H, m), 1.35 (12H, s), 1.59 (1H, m), 2.30 (3H, s), 5.70 (1H, dd), 7.13-7.26 (2H, m), 7.41 (1H, d), 7.54 (1H, s).

Intermediate compound 61: $^1$H-NMR (CDCl$_3$) δ: 0.49 (2H, m), 0.78 (2H, m), 1.41 (12H, s), 1.51 (1H, m), 2.39 (3H, s), 5.65 (1H, dd), 6.70 (1H, d), 6.95 (1H, m), 7.12-7.23 (2H, m).

Intermediate compound 63: $^1$H-NMR (CDCl$_3$) δ: 0.52 (1H, t), 0.75 (1H, dd), 1.14 (6H, s), 1.35 (12H, s), 1.44 (1H, m), 2.33 (3H, s), 5.99 (1H, dd), 6.98 (1H, d), 7.23 (1H, d), 7.34 (1H, s), 7.65 (1H, d).

Intermediate compound 64: $^1$H-NMR (CDCl$_3$) δ: 0.57 (1H, m), 0.70 (1H, m), 0.90 (1H, m), 1.12 (3H, d), 1.28 (1H, m), 1.35 (12H, s), 2.31 (3H, s), 5.77 (1H, dd), 6.97 (1H, dd), 7.20 (1H, d), 7.30 (1H, s), 7.64 (1H, d).

Intermediate compound 65: $^1$H-NMR (CDCl$_3$) δ: 0.54 (1H, t), 0.78 (1H, dd), 1.14 (3H, s), 1.15 (3H, s), 1.35 (12H, s), 1.45 (1H, m), 5.99 (1H, dd), 6.84 (1H, m), 7.19 (1H, m), 7.25 (1H, dd), 7.74 (1H, m).

Intermediate compound 66: $^1$H-NMR (CDCl$_3$) δ: 0.54 (1H, t), 0.78 (1H, dd), 1.14 (3H, s), 1.15 (3H, s), 1.35 (12H, s), 1.44 (1H, m), 6.00 (1H, dd), 7.12 (1H, dd), 7.20 (1H, d), 7.48 (1H, d), 7.67 (1H, d).

Preparation Example 1

To a mixture of the intermediate compound 1 0.7 g, THF 6 mL and DMF 6 mL was added sodium hydride (60%, oily) 0.29 g at 0° C., followed by methyl formate 0.6 mL, and the mixture was stirred for 1 hour. To the resulting mixture was added 2M hydrochloric acid, and the mixture was extracted with MTBE. The resulting organic layer was dried over anhydrous magnesium sulfate, filtered, and concentrated under reduced pressure. The resulting residue was solubilized with THE 8 mL and DMF 4 mL, and thereto were added potassium carbonate 0.54 g, and methyl iodide 0.55 g successively, and the mixture was stirred for 1 hour. To the resulting mixture was added saturated aqueous ammonium chloride solution, and the mixture was extracted with MTBE. The resulting organic layer was dried over anhydrous magnesium sulfate, filtered, and concentrated under reduced pressure. The residue was subjected to a silica gel column chromatography (hexane:ethyl acetate=5:1) to obtain the present compound 1 represented by the below-mentioned formula 0.52 g.

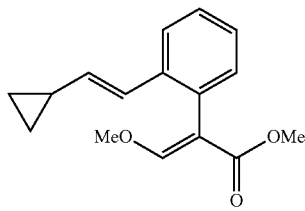 [SMILES: CO/C=C(/C(=O)OC)c1ccccc1/C=C/C1CC1]

Present invention 1: $^1$H-NMR (CDCl$_3$) δ: 0.46 (2H, m), 0.78 (2H, m), 1.50 (1H, m), 3.69 (3H, s), 3.82 (3H, s), 5.64 (1H, dd), 6.40 (1H, d), 7.10 (1H, d), 7.17-7.26 (2H, m), 7.48 (1H, d), 7.59 (1H, s).

The compounds which were prepared according to a similar method to that described in the Preparation example 1, and their physical properties are shown below.

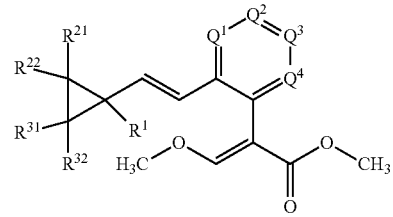

wherein a combination of $R^1$, $R^{21}$, $R^{22}$, $R^{31}$, $R^{32}$, $Q^1$, $Q^2$, $Q^3$, and $Q^4$ represents any combinations indicated in [Table 14].

TABLE 14

| Present compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 2 | H | H | H | H | H | CH | CF | CH | CH |
| 3 | H | H | H | H | H | CH | CH | CCl | CH |
| 6 | H | H | H | H | H | CH | CCl | CH | CH |
| 10 | H | H | H | H | H | CH | COMe | CH | CH |

Present compound 2: $^1$H-NMR (CDCl$_3$) δ: 0.48 (2H, m), 0.81 (2H, m), 1.53 (1H, m), 3.70 (3H, s), 3.83 (3H, s), 5.63 (1H, dd), 6.34 (1H, d), 6.89 (1H, dd), 7.05 (1H, dd), 7.15 (1H, d), 7.59 (1H, s).

Present compound 3: $^1$H-NMR (CDCl$_3$) δ:0.47 (2H, m), 0.79 (2H, m), 1.50 (1H, m), 3.70 (3H, s), 3.84 (3H, s), 5.62 (1H, dd), 6.32 (1H, d), 7.08 (1H, s), 7.19 (1H, d), 7.39 (1H, d), 7.58 (1H, s).

Present compound 6: $^1$H-NMR (CDCl$_3$) δ: 0.49 (2H, m), 0.83 (2H, m), 4.54 (1H, m), 3.69 (3H, s), 3.83 (3H, s), 5.64 (1H, dd), 6.32 (1H, d), 7.02 (1H, d), 7.14 (1H, d), 7.44 (1H, s), 7.58 (1H, s).

Present compound 10: $^1$H-NMR (CDCl$_3$) δ:0.48 (2H, m), 0.79 (2H, m), 1.52 (1H, m), 3.69 (3H, s), 3.81 (3H, s), 3.82 (3H, s), 5.63 (1H, dd), 6.36 (1H, d), 6.76 (1H, d), 6.99-7.04 (2H, m), 7.57 (1H, s).

Preparation Example 2

A mixture of the intermediate compound 51 0.57 g, methyl (2Z)-2-iodo-3-methoxyacrylate 0.34 g, tripotassium phosphate 0.90 g, tetrakis(triphenylphosphine)palladium (0) 0.17 g, 1,4-dioxane 8 mL, and water 2 mL was stirred under reflux under nitrogen atmosphere for 23 hours. The resulting mixture was cooled to room temperature, and thereto was then added MTBE, and the mixture was washed with saturated aqueous ammonium chloride solution, and saturated brine successively. The resulting organic layer was dried over anhydrous magnesium sulfate, filtered, and concentrated under reduced pressure. The residue was subjected to silica gel column chromatography (hexane:ethyl acetate=5:1) to obtain the present compound 4 represented by the below-mentioned formula 0.24 g.

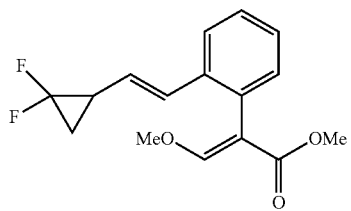 [SMILES: CO/C=C(/C(=O)OC)c1ccccc1/C=C/C1CC1(F)F]

Present compound 4: ¹H-NMR (CDCl₃) δ: 1.30 (1H, m), 1.67 (1H, m), 2.34 (1H, m), 3.69 (3H, s), 3.82 (3H, s), 5.82 (1H, m), 6.53 (1H, d), 7.13 (1H, dd), 7.25 (1H, td), 7.28 (1H, td), 7.51 (1H, dd), 7.60 (1H, s).

The compounds which were prepared according to a similar method to that described in the Preparation example 2, and their physical properties are shown below.

A compound represented by formula (I):

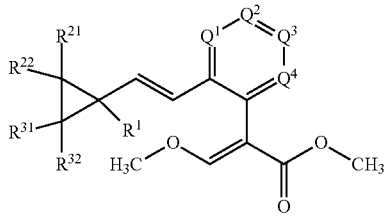

(I)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 15].

TABLE 15

| Present compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 5 | H | H | H | H | H | CCl | CH | CH | CH |
| 7 | H | H | H | H | H | CH | CMe | CH | CH |
| 8 | H | H | H | H | H | CH | CEt | CH | CH |
| 9 | H | H | H | H | H | CH | CCF₃ | CH | CH |
| 11 | H | H | H | H | H | CH | CH | CMe | CH |
| 12 | H | H | H | H | H | CH | CH | CH | CMe |
| 13 | Me | H | H | H | H | CH | CH | CH | CH |
| 14 | H | Me | H | H | H | CH | CH | CH | CH |
| 15 | H | Me | Me | H | H | CH | CH | CH | CH |
| 16 | H | Me | Me | Me | Me | CH | CH | CH | CH |
| 17 | H | Me | H | H | H | CH | CMe | CH | CH |
| 18 | H | Me | Me | H | H | CH | CF | CH | CH |
| 19 | H | Me | Me | H | H | CH | CCl | CH | CH |
| 20 | H | Me | Me | H | H | CH | CMe | CH | CH |
| 21 | H | Me | Me | H | H | CH | COMe | CH | CH |
| 22 | H | H | H | H | H | N | CH | CH | CH |

Present compound 5: ¹H-NMR (CDCl₃) δ: 0.42 (2H, m), 0.75 (2H, m), 1.50 (1H, m), 3.67 (3H, s), 3.83 (3H, s), 5.39 (1H, dd), 6.37 (1H, d), 7.06-7.13 (2H, m), 7.30 (1H, d), 7.41 (1H, s).

Present compound 7: ¹H-NMR (CDCl₃) δ: 0.46 (2H, m), 0.77 (2H, m), 1.51 (1H, m), 2.32 (3H, s), 3.69 (3H, s), 3.82 (3H, s), 5.63 (1H, dd), 6.37 (1H, d), 7.00 (2H, s), 7.29 (1H, s), 7.57 (1H, s).

Present compound 8: ¹H-NMR (CDCl₃) δ: 0.47 (2H, m), 0.77 (2H, m), 1.24 (3H, t), 1.52 (1H, m), 2.63 (2H, q), 3.69 (3H, s), 3.82 (3H, s), 5.64 (1H, dd), 6.38 (1H, d), 7.03 (2H, s), 7.31 (1H, s), 7.57 (1H, s).

Present compound 9: ¹H-NMR (CDCl₃) δ: 0.51 (2H, m), 0.82 (2H, m), 1.54 (1H, m), 3.70 (3H, s), 3.85 (3H, s), 5.70 (1H, dd), 6.39 (1H, d), 7.21 (1H, d), 7.41 (1H, d), 7.61 (1H, s), 7.70 (1H, s).

Present compound 11: ¹H-NMR (CDCl₃) δ: 0.45 (2H, m), 0.77 (2H, m), 1.51 (1H, m), 2.31 (3H, s), 3.69 (3H, s), 3.82 (3H, s), 5.59 (1H, dd), 6.36 (1H, d), 6.91 (1H, s), 7.04 (1H, d), 7.37 (1H, d), 7.57 (1H, s).

Present compound 12: ¹H-NMR (CDCl₃) δ: 0.45 (2H, m), 0.77 (2H, m), 1.51 (1H, m), 2.15 (3H, s), 3.68 (3H, s), 3.81 (3H, s), 5.60 (1H, dd), 6.42 (1H, d), 7.06-7.33 (3H, m), 7.61 (1H, s).

Present compound 13: ¹H-NMR (CDCl₃) δ: 0.62-0.68 (4H, m), 1.22 (3H, s), 3.68 (3H, s), 3.82 (3H, s), 5.76 (1H, d), 6.25 (1H, d), 7.12 (1H, dd), 7.18 (1H, td), 7.24 (1H, m), 7.48 (1H, m), 7.58 (1H, s).

Present compound 14: ¹H-NMR (CDCl₃) δ: 0.55 (1H, m), 0.64 (1H, m), 0.86 (1H, m), 1.09 (3H, d), 1.22 (1H, m), 3.69 (3H, s), 3.82 (3H, s), 5.68 (1H, dd), 6.34 (1H, d), 7.09 (1H, dd), 7.18 (1H, td), 7.23 (1H, m), 7.47 (1H, dd), 7.58 (1H, s).

Present compound 15: ¹H-NMR (CDCl₃) δ: 0.45 (1H, t), 0.74 (1H, dd), 1.10 (6H, s), 1.38 (1H, m), 3.69 (3H, s), 3.82 (3H, s), 5.90 (1H, dd), 6.39 (1H, d), 7.10 (1H, dd), 7.18 (1H, td), 7.25 (1H, td), 7.50 (1H, dd), 7.58 (1H, s). Present compound 16: ¹H-NMR (CDCl₃) δ: 1.07 (1H, d), 1.07 (6H, s), 1.13 (6H, s), 3.69 (3H, s), 3.81 (3H, s), 5.94 (1H, dd), 6.39 (1H, d), 7.10 (1H, dd), 7.18 (1H, td), 7.25 (1H, td), 7.50 (1H, d), 7.58 (1H, s).

Present compound 17: ¹H-NMR (CDCl₃) δ: 0.54 (1H, m), 0.63 (1H, m), 0.84 (1H, m), 1.09 (3H, d), 1.21 (1H, m), 2.32 (3H, s), 3.68 (3H, s), 3.81 (3H, s), 5.66 (1H, dd), 6.31 (1H, d), 6.99-7.00 (2H, m), 7.28 (1H, br s), 7.57 (1H, s).

Present compound 18: ¹H-NMR (CDCl₃) δ: 0.48 (1H, t), 0.76 (1H, dd), 1.11 (6H, s), 1.38 (1H, m), 3.69 (3H, s), 3.82 (3H, s), 5.90 (1H, dd), 6.32 (1H, dd), 6.88 (1H, m), 7.05 (1H, m), 7.17 (1H, m), 7.59 (1H, s).

Present compound 19: ¹H-NMR (CDCl₃) δ: 0.48 (1H, t), 0.76 (1H, dd), 1.11 (3H, s), 1.12 (3H, s), 1.37 (1H, m), 3.69 (3H, s), 3.83 (3H, s), 5.90 (1H, dd), 6.30 (1H, d), 7.03 (1H, d), 7.14 (1H, dd), 7.46 (1H, d), 7.58 (1H, s).

Present compound 20: ¹H-NMR (CDCl₃) δ: 0.45 (1H, t), 0.73 (1H, dd), 1.10 (6H, s), 1.37 (1H, m), 2.33 (3H, s), 3.68 (3H, s), 3.81 (3H, s), 5.88 (1H, dd), 6.35 (1H, d), 6.98-7.03 (2H, m), 7.31 (1H, br s), 7.57 (1H, s).

Present compound 21: ¹H-NMR (CDCl₃) δ: 0.46 (1H, t), 0.74 (1H, dd), 1.10 (6H, s), 1.37 (1H, m), 3.69 (3H, s), 3.81 (3H, s), 3.82 (3H, s), 5.89 (1H, dd), 6.34 (1H, d), 7.02 (1H, d), 7.03 (2H, m), 7.57 (1H, s).

Present compound 22: ¹H-NMR (CDCl₃) δ: 0.60 (2H, m), 0.83 (2H, m), 1.57 (1H, m), 3.70 (3H, s), 3.85 (3H, s), 6.40-6.50 (2H, m), 7.08 (1H, dd), 7.39 (1H, d), 7.625 (1H, s), 8.45 (1H, d).

Preparation Example 3

A mixture of the intermediate compound 6 0.81 g, methyl orthoformate 12.5 mL, acetic anhydride 2.3 mL, and zinc chloride 17 mg was stirred under reflux for 23 hours. The resulting mixture was cooled to room temperature, and thereto was then added ethyl acetate, and the mixture was washed with saturated aqueous sodium hydrogen carbonate solution and water. The resulting organic layer was dried anhydrous magnesium sulfate, filtered, and concentrated under reduced pressure. The resulting residue was subjected to a silica gel column chromatography (hexane:ethyl acetate=1:1) to obtain the present compound 23 represented by the below mentioned formula 0.32 g.

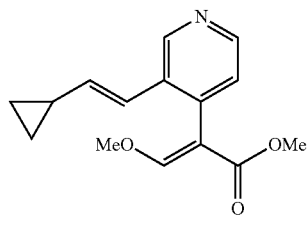 [SMILES: CO/C=C(/C(=O)OC)c1ccncc1/C=C/C1CC1]

Present compound 23: $^1$H-NMR (CDCl$_3$) δ: 0.51 (2H, m), 0.82 (2H, m), 1.52 (1H, m), 3.70 (3H, s), 3.85 (3H, s), 5.71 (1H, dd), 6.31 (1H, d), 7.01 (1H, d), 7.59 (1H, d), 8.38 (1H, d), 8.68 (1H, s).

The compounds which were prepared according to a similar method to that described in the Preparation example 3, and their physical properties are shown below.

A compound represented by formula (I):

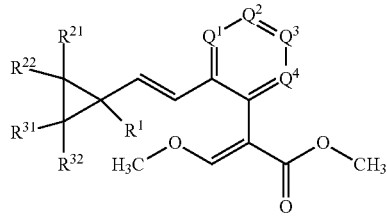

(I)

wherein a combination of $R^1$, $R^{21}$, $R^{22}$, $R^{31}$, $R^{32}$, $Q^1$, $Q^2$, $Q^3$, and $Q^4$ represents any combinations indicated in [Table 16].

TABLE 16

| Present compound | $R^1$ | $R^{21}$ | $R^{22}$ | $R^{31}$ | $R^{32}$ | $Q^1$ | $Q^2$ | $Q^3$ | $Q^4$ |
|---|---|---|---|---|---|---|---|---|---|
| 24 | H | H | H | H | H | CH | CH | CH | N |

Present compound 24: $^1$H-NMR (CDCl$_3$) δ: 0.50 (2H, m), 0.82 (2H, m), 1.55 (1H, m), 3.70 (3H, s), 3.85 (3H, s), 5.68 (1H, dd), 6.38 (1H, d), 7.19 (1H, m), 7.65 (1H, s), 7.77 (1H, d), 8.50 (1H, br s).

Next, examples of the present compounds which are prepared according to either the Preparation Examples described in Examples or the Process described herein are shown below.

A compound represented by formula (L-1)

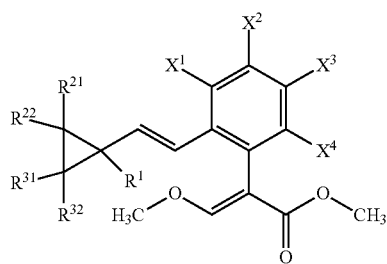

(L-1)

wherein $X^1$, $X^2$, $X^3$, and $X^4$ represent a hydrogen atom, and a combination of $R^1$, $R^{21}$, $R^{22}$, $R^{31}$ and $R^{32}$ represents any combinations listed in Table 17 (hereinafter, referred to as "Compound class SX1").

TABLE 17

| $R^1$ | $R^{21}$ | $R^{22}$ | $R^{31}$ | $R^{32}$ |
|---|---|---|---|---|
| H | H | H | H | H |
| H | Me | H | H | H |
| H | Me | Me | H | H |
| H | Me | H | Me | H |
| H | Me | Me | Me | H |
| H | Me | Me | Me | Me |

TABLE 17-continued

| $R^1$ | $R^{21}$ | $R^{22}$ | $R^{31}$ | $R^{32}$ |
|---|---|---|---|---|
| H | CF$_3$ | H | H | H |
| H | CH=CH$_2$ | H | H | H |
| H | C≡CH | H | H | H |
| H | Me | Me | CH=CMe$_2$ | H |
| H | Me | Me | CH=CCl$_2$ | H |
| H | F | H | H | H |
| H | F | F | H | H |
| H | F | Cl | H | H |
| H | Cl | Cl | H | H |
| Me | H | H | H | H |
| Me | Me | H | H | H |

A compound (L-1) wherein $X^1$, $X^3$ and $X^4$ represent a hydrogen atom, $X^2$ represents a methyl group, and a combination of $R^1$, $R^{21}$, $R^{22}$, $R^{31}$ and $R^{32}$ represents any combinations listed in [Table 17] (hereinafter, referred to as "Compound Class SX2").

A compound (L-1) wherein $X^1$, $X^3$ and $X^4$ represent a hydrogen atom, $X^2$ represents an ethyl group, and a combination of $R^1$, $R^{21}$, $R^{22}$, $R^{31}$ and $R^{32}$ represents any combinations listed in [Table 17] (hereinafter, referred to as "Compound Class SX3").

A compound (L-1) wherein $X^1$, $X^3$ and $X^4$ represent a hydrogen atom, $X^2$ represents a propyl group, and a combination of $R^1$, $R^{21}$, $R^{22}$, $R^{31}$ and $R^{32}$ represents any combinations listed in [Table 17] (hereinafter, referred to as "Compound Class SX4").

A compound (L-1) wherein $X^1$, $X^3$ and $X^4$ represent a hydrogen atom, $X^2$ represents an isopropyl group, and a combination of $R^1$, $R^{21}$, $R^{22}$, $R^{31}$ and $R^{32}$ represents any combinations listed in [Table 17] (hereinafter, referred to as "Compound Class SX5").

A compound (L-1) wherein $X^1$, $X^3$ and $X^4$ represent a hydrogen atom, $X^2$ represents a butyl group, and a combination of $R^1$, $R^{21}$, $R^{22}$, $R^{31}$ and $R^{32}$ represents any combinations listed in [Table 17] (hereinafter, referred to as "Compound Class SX6").

A compound (L-1) wherein $X^1$, $X^3$ and $X^4$ represent a hydrogen atom, $X^2$ represents a tert-butyl group, and a combination of $R^1$, $R^{21}$, $R^{22}$, $R^{31}$ and $R^{32}$ represents any combinations listed in [Table 17] (hereinafter, referred to as "Compound Class SX7").

A compound (L-1) wherein $X^1$, $X^3$ and $X^4$ represent a hydrogen atom, $X^2$ represents a vinyl group, and a combination of $R^1$, $R^{21}$, $R^{22}$, $R^{31}$ and $R^{32}$ represents any combinations listed in [Table 17] (hereinafter, referred to as "Compound Class SX8").

A compound (L-1) wherein $X^1$, $X^3$ and $X^4$ represent a hydrogen atom, $X^2$ represents an ethynyl group, and a combination of $R^1$, $R^{21}$, $R^{22}$, $R^{31}$ and $R^{32}$ represents any combinations listed in [Table 17] (hereinafter, referred to as "Compound Class SX9").

A compound (L-1) wherein $X^1$, $X^3$ and $X^4$ represent a hydrogen atom, $X^2$ represents a fluorine atom, and a combination of $R^1$, $R^{21}$, $R^{22}$, $R^{31}$ and $R^{32}$ represents any combinations listed in [Table 17] (hereinafter, referred to as "Compound Class SX10").

A compound (L-1) wherein $X^1$, $X^3$ and $X^4$ represent a hydrogen atom, $X^2$ represents a chlorine atom, and a combination of $R^1$, $R^{21}$, $R^{22}$, $R^{31}$ and $R^{32}$ represents any combinations listed in [Table 17] (hereinafter, referred to as "Compound Class SX11").

A compound (L-1) wherein $X^1$, $X^3$ and $X^4$ represent a hydrogen atom, $X^2$ represents a bromine atom, and a combination of $R^1$, $R^{21}$, $R^{22}$, $R^{31}$ and $R^{32}$ represents any combinations listed in [Table 17] (hereinafter, referred to as "Compound Class SX12").

A compound (L-1) wherein $X^1$, $X^3$ and $X^4$ represent a hydrogen atom, $X^2$ represents an iodine atom, and a combination of $R^1$, $R^{21}$, $R^{22}$, $R^{31}$ and $R^{32}$ represents any combinations listed in [Table 17] (hereinafter, referred to as "Compound Class SX13").

A compound (L-1) wherein $X^1$, $X^3$ and $X^4$ represent a hydrogen atom, $X^2$ represents a methoxy group, and a combination of $R^1$, $R^{21}$, $R^{22}$, $R^{31}$ and $R^{32}$ represents any combinations listed in [Table 17] (hereinafter, referred to as "Compound Class SX14").

A compound (L-1) wherein $X^1$, $X^3$ and $X^4$ represent a hydrogen atom, $X^2$ represents an ethoxy group, and a combination of $R^1$, $R^{21}$, $R^{22}$, $R^{31}$ and $R^{32}$ represents any combinations listed in [Table 17] (hereinafter, referred to as "Compound Class SX15").

A compound (L-1) wherein $X^1$, $X^3$ and $X^4$ represent a hydrogen atom, $X^2$ represents a propoxy group, and a combination of $R^1$, $R^{21}$, $R^{22}$, $R^{31}$ and $R^{32}$ represents any combinations listed in [Table 17] (hereinafter, referred to as "Compound Class SX16").

A compound (L-1) wherein $X^1$, $X^3$ and $X^4$ represent a hydrogen atom, $X^2$ represents a butoxy group, and a combination of $R^1$, $R^{21}$, $R^{22}$, $R^{31}$ and $R^{32}$ represents any combinations listed in [Table 17] (hereinafter, referred to as "Compound Class SX17").

A compound (L-1) wherein $X^1$, $X^3$ and $X^4$ represent a hydrogen atom, $X^2$ represents a difluoromethyl group, and a combination of $R^1$, $R^{21}$, $R^{22}$, $R^{31}$ and $R^{32}$ represents any combinations listed in [Table 17] (hereinafter, referred to as "Compound Class SX18").

A compound (L-1) wherein $X^1$, $X^3$ and $X^4$ represent a hydrogen atom, $X^2$ represents a trifluoromethyl group, and a combination of $R^1$, $R^{21}$, $R^{22}$, $R^{31}$ and $R^{32}$ represents any combinations listed in [Table 17] (hereinafter, referred to as "Compound Class SX19").

A compound (L-1) wherein $X^1$, $X^3$ and $X^4$ represent a hydrogen atom, $X^2$ represents a methoxymethyl group, and a combination of $R^1$, $R^{21}$, $R^{22}$, $R^{31}$ and $R^{32}$ represents any combinations listed in [Table 17] (hereinafter, referred to as "Compound Class SX20").

A compound (L-1) wherein $X^1$, $X^3$ and $X^4$ represent a hydrogen atom, $X^2$ represents a difluoromethoxy group, and a combination of $R^1$, $R^{21}$, $R^{22}$, $R^{31}$ and $R^{32}$ represents any combinations listed in [Table 17] (hereinafter, referred to as "Compound Class SX21").

A compound (L-1) wherein $X^1$, $X^3$ and $X^4$ represent a hydrogen atom, $X^2$ represents a trifluoromethoxy group, and a combination of $R^1$, $R^{21}$, $R^{22}$, $R^{31}$ and $R^{32}$ represents any combinations listed in [Table 17] (hereinafter, referred to as "Compound Class SX22").

A compound (L-1) wherein $X^2$, $X^3$ and $X^4$ represent a hydrogen atom, XI represents a methyl group, and a combination of $R^1$, $R^{21}$, $R^{22}$, $R^{31}$ and $R^{32}$ represents any combinations listed in [Table 17] (hereinafter, referred to as "Compound Class SX23").

A compound (L-1) wherein $X^1$, $X^2$ and $X^4$ represent a hydrogen atom, $X^3$ represents a methyl group, and a combination of $R^1$, $R^{21}$, $R^{22}$, $R^{31}$ and $R^{32}$ represents any combinations listed in [Table 17] (hereinafter, referred to as "Compound Class SX24").

A compound (L-1) wherein $X^1$, $X^2$ and $X^3$ represent a hydrogen atom, $X^4$ represents a methyl group, and a combination of $R^1$, $R^{21}$, $R^{22}$, $R^{31}$ and $R^{32}$ represents any combinations listed in [Table 17] (hereinafter, referred to as "Compound Class SX25").

A compound (L-1) wherein $X^2$, $X^3$ and $X^4$ represent a hydrogen atom, $X^4$ represents a fluorine atom, and a combination of $R^1$, $R^{21}$, $R^{22}$, $R^{31}$ and $R^{32}$ represents any combinations listed in [Table 17] (hereinafter, referred to as "Compound Class SX26").

A compound (L-1) wherein $X^1$, $X^2$ and $X^4$ represent a hydrogen atom, $X^3$ represents a fluorine atom, and a combination of $R^1$, $R^{21}$, $R^{22}$, $R^{31}$ and $R^{32}$ represents any combinations listed in [Table 17] (hereinafter, referred to as "Compound Class SX27").

A compound (L-1) wherein $X^1$, $X^2$ and $X^3$ represent a hydrogen atom, $X^3$ represents a fluorine atom, and a combination of $R^1$, $R^{21}$, $R^{22}$, $R^{31}$ and $R^{32}$ represents any combinations listed in [Table 17] (hereinafter, referred to as "Compound Class SX28").

A compound (L-1) wherein $X^2$, $X^3$ and $X^4$ represent a hydrogen atom, $X^1$ represents a chlorine atom, and a combination of $R^1$, $R^{21}$, $R^{22}$, $R^{31}$ and $R^{32}$ represents any combinations listed in [Table 17] (hereinafter, referred to as "Compound Class SX29").

A compound (L-1) wherein $X^1$, $X^2$ and $X^4$ represent a hydrogen atom, $X^3$ represents a chlorine atom, and a combination of $R^1$, $R^{21}$, $R^{22}$, $R^{31}$ and $R^{32}$ represents any combinations listed in [Table 17] (hereinafter, referred to as "Compound Class SX30").

A compound (L-1) wherein $X^1$, $X^2$ and $X^3$ represent a hydrogen atom, $X^3$ represents a chlorine atom, and a combination of $R^1$, $R^{21}$, $R^{22}$, $R^{31}$ and $R^{32}$ represents any combinations listed in [Table 17] (hereinafter, referred to as "Compound Class SX31").

A compound (L-1) wherein $X^2$, $X^3$ and $X^4$ represent a hydrogen atom, $X^1$ represents a methoxy group, and a combination of $R^1$, $R^{21}$, $R^{22}$, $R^{31}$ and $R^{32}$ represents any combinations listed in [Table 17] (hereinafter, referred to as "Compound Class SX32).

A compound (L-1) wherein $X^1$, $X^2$ and $X^4$ represent a hydrogen atom, $X^3$ represents a methoxy group, and a combination of $R^1$, $R^{21}$, $R^{22}$, $R^{31}$ and $R^{32}$ represents any combinations listed in [Table 17] (hereinafter, referred to as "Compound Class SX33").

A compound (L-1) wherein $X^1$, $X^2$ and $X^3$ represent a hydrogen atom, $X^4$ represents a methoxy group, and a combination of $R^1$, $R^{21}$, $R^{22}$, $R^{31}$ and $R^{32}$ represents any combinations listed in [Table 17] (hereinafter, referred to as "Compound Class SX34").

A compound (L-1) wherein $X^1$ and $X^4$ represent a hydrogen atom, $X^2$ and $X^3$ represent a methyl group, and a combination of $R^1$, $R^{21}$, $R^{22}$, $R^{31}$ and $R^{32}$ represents any combinations listed in [Table 17] (hereinafter, referred to as "Compound Class SX35").

A compound (L-1) wherein $X^1$ and $X^3$ represent a hydrogen atom, $X^2$ and $X^4$ represent a methyl group, and a combination of $R^1$, $R^{21}$, $R^{22}$, $R^{31}$ and $R^{32}$ represents any combinations listed in [Table 17] (hereinafter, referred to as "Compound Class SX36").

A compound (L-1) wherein $X^1$ represents a fluorine atom, $X^2$ represents a methyl group, $X^3$ and $X^4$ represent a hydrogen atom, and a combination of $R^1$, $R^{21}$, $R^{22}$, $R^{31}$ and $R^{32}$ represents any combinations listed in [Table 17](hereinafter, referred to as "Compound Class SX37").

A compound (L-1) wherein $X^1$ represents a fluorine atom, $X^2$ represents a chlorine atom, $X^3$ and $X^4$ represent a hydrogen atom, and a combination of $R^1$, $R^{21}$, $R^{22}$, $R^{31}$ and $R^{32}$ represents any combinations listed in [Table 17](hereinafter, referred to as "Compound Class SX38").

A compound represented by formula (L-2):

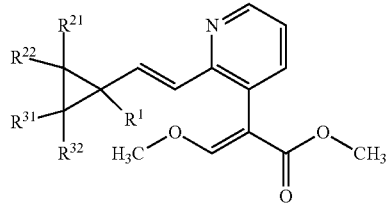
(L-2)

(hereinafter, referred to as "Compound (L-2)")
wherein a combination of $R^1$, $R^{21}$, $R^{22}$, $R^{31}$ and $R^{32}$ represents any combinations listed in Table 17 (hereinafter, referred to as "Compound Class SX39")

A compound represented by formula (L-3):

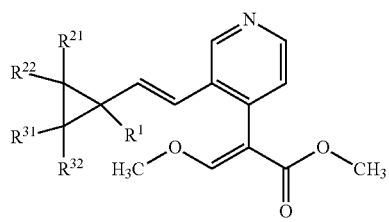
(L-3)

(hereinafter, referred to as "Compound (L-3)")
wherein a combination of $R^1$, $R^{21}$, $R^{22}$, $R^{31}$ and $R^{32}$ represents any combinations listed in Table 17 (hereinafter, referred to as "Compound Class SX40").

A compound represented by formula (L-4):

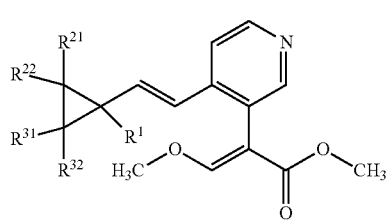
(L-4)

(hereinafter, referred to as "Compound (L-4)")
wherein a combination of $R^1$, $R^{21}$, $R^{22}$, $R^{31}$ and $R^{32}$ represents any combinations listed in Table 17 (hereinafter, referred to as "Compound Class SX41").

A compound represented by formula (L-5):

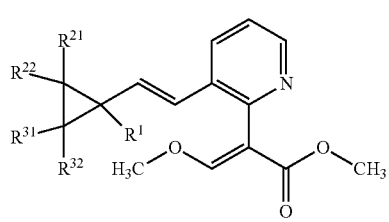
(L-5)

(hereinafter, referred to as "Compound (L-5)")
wherein a combination of $R^1$, $R^{21}$, $R^{22}$, $R^{31}$ and $R^{32}$ represents any combinations listed in Table 17 (hereinafter, referred to as "Compound Class SX42").

Next, the Formulation examples of the present compound X are shown below. The "parts" represents "part by weight". Further, the present compound S represents the compounds described as the compound groups SX1 to SX42.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 7

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 8

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60, and 50 parts of distilled water are filled into an aerosol container, and a valve part of the container is attached. Then, 40 parts of LPG is filled therein through the valve under pressure to obtain each aqueous aerosol.

Formulation Example 10

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 12

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 13

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 16

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 17

To a mixture of 57 parts of fractional distilled palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 18

Five (5) parts of any one of the present compounds S is mixed with 95 parts of limestone filler, followed by a wet-granulation of the resulting mixture to obtain each granule for oral administration.

Formulation Example 19

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 21

To 0.1 parts of any one of the present compounds S, 40 parts of sodium polyoxyethylene lauryl ether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 22

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 23

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, an efficacy of the present compound on controlling harmful arthropods is shown by Test examples. The following tests were conducted at 25° C.

Test Method 1

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cucumber (*Cucumber sativus*) seedling (on the developmental stage of the second true leaf) is planted in a cup, and approximately 30 cotton aphids (*Aphis gossypii*) (all stages of life) are released onto the seedling. After one day, the diluted solutions are sprayed into the seedling at a ratio of 10 mL/seedling. After 5 days, the number of the surviving insects is examined and the controlling value is calculated by the following equation.

Controlling value (%)={1−(Cb×Tai)/(Cai×Tb)}×100 wherein the symbols in the equation represent the following descriptions.
Cb: Number of the test insects in untreated group;
Cai: Number of the surviving insects at the time of the examination in untreated group;
Tb: Number of the test insects in treated group;
Tai: Number of the surviving insects at the time of the examination in treated group;
Here the "untreated group" represents a group where a similar treatment procedure to that of treated group except not using the test compound is done.

Test Example 1

The test was conducted according to the Test method 1 by making the prescribed concentration 500 ppm and using the below-mentioned present compounds as a test compound, and, as the result of the test, the below-mentioned present compounds showed 90% or more as the controlling value.
Present compound(s): 1, 2, 3, 4, 5, 6, 8, 9, 10, 11, 12, 13, 14, 15, 16, 17, 19, 20 and 22

Test Method 2

The test compounds are made to a formulation according to the method described in the Formulation Example 5, and thereto was is water to prepare a diluted solution containing a prescribed concentration of the test compound.

In a container, 7.7 g of artificial diet (Insecta LF, manufactured by NOSAN CORPORATION) is placed, and 2 mL of the diluted solution is irrigated thereto. Five (5) fourth instar larvae of tobacco cutworm (*Spodoptera litura*) are released onto the artificial diet. After 5 days, the number of the surviving insects is examined, and the mortality of insects is calculated by the following equation.

Mortality (%)={1−the number of the surviving insects/5}×100

Test Example 2

The test was conducted by making the prescribed concentration 500 ppm and using the below-mentioned present compounds as a test compound according to the test method 2. As a result of the test, the below-mentioned present compounds showed 80% or greater as the mortality.
Present compound(s): 1, 2, 3, 4, 5, 6, 7, 8, 9, 10, 11, 12, 13, 14, 15, 16, 17, 19, 20 and 22

Test Method 3

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) diamondback moth (*Plutella xylostella*) at the second instar larval stage are released into the cup. After 5 days, the number of the surviving insects is counted, and the mortality of insects is calculated by the following equation.

Mortality (%)=(1−Number of surviving insects/5)×100

Test Example 3

The test was conducted according to the Test method 3 by making the prescribed concentration 500 ppm and using the below-mentioned present compounds as a test compound, and, as the result of the test, the below-mentioned present compounds showed 80% or more as the mortality of insects.
Present compound(s): 1, 2, 3, 4, 5, 6, 7, 8, 9, 10, 11, 12, 13, 14, 15, 16, 17, 19, 20, and 22

Test Method 4

The test compounds are made to a formulation according to the method described in the Formulation Example 5, and thereto was added water containing 0.03 v/v % of Shindain (registered trademark) to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 of 3rd instar larvae of brown planthopper (*Nilaparvata lugens*) are released onto the rice leaves. After 6 days, the number of the surviving insects is examined, and the mortality is calculated by the following equation.

Mortality (%)={1−the number of the surviving insects/20}×100

Test Example 4

The test was conducted according to the Test method 4 by making the prescribed concentration 500 ppm and using the below-mentioned present compounds as a test compound, and, as the result of the test, the below-mentioned present compounds showed 90% or more as the mortality of insects.
Present compound(s): 1, 2, 3, 4, 5, 6, 7, 8, 9, 10, 11, 12, 13, 14, 15, 17, 19, 20, and 22

Test Method 5

The test compounds are made to a formulation according to a similar method to that described in the Formulation Example 5, and thereto is added water containing 0.03 v/v % of Shindain (registered trademark) to prepare a diluted solution containing a prescribed concentration of the test compound.

Silverleaf whiteflies (*Bemisia tabaci*) are released on tomato (*Lycopersicon esculentum*) seedling that is planted in the container, and then spawn for about 24 hours. The seedling are stored for 8 days, and the larvae of silverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

$$\text{Controlling value (\%)} = \{1 - (Cb \times Tai)/(Cai \times Tb)\} \times 100$$

wherein the symbols in the formula represent the following descriptions.
- Cb: Number of the insects shortly before the treatment in untreated group;
- Cai: Number of the surviving insects at the time of the investigation in untreated group;
- Tb: Number of the insects shortly before the treatment in treated group;
- Tai: Number of the surviving insects at the time of the investigation in treated group;

Here the "untreated group" represents a group where the similar treatment procedure to that of the treated group except not using the test compound is done.

Test Method 6

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cucumber (*Cucumber sativus*) seedling (on the developmental stage of the second leaf) is planted in a cup, and the diluted solutions are sprayed into the seedling at a ratio of 10 mL/seedling. Thereafter, the first true leaf thereof is cut out and then is installed into a cup, and about twenty (20) instar larvae of Western flower thrips (*Frankliniella occidentalis*) are released. After 7 days, the number of the surviving insects is examined, and the controlling value is calculated by the following equation.

$$\text{Mortality (\%)} = \{1 - \text{the number of the surviving insects}/20\} \times 100$$

Test Method 7

The test compounds are made to a formulation according to a similar method to that described in the Formulation Example 5, and thereto is added water containing 0.03 v/v % of Shindain (registered trademark) to prepare a diluted solution containing a prescribed concentration of the test compound. Kidney bean (*Phaseolus vulgaris*) seedling (on the developmental stage of the first true leaf) is planted in a cup, and about forty (40) adult female of common red spider mite (*Tetranychus urticae*) are released. After 1 day, the diluted solutions are sprayed into the seedling at a ratio of 10 mL/seedling. Further, after 7 days, the number of the surviving insects is examined, and the controlling value is calculated by the following equation.

$$\text{Controlling value (\%)} = \{1 - (Cb \times Tai)/(Cai \times Tb)\} \times 100$$

wherein the symbols in the equation represent the following descriptions.
- Cb: Number of the test insects in untreated group;
- Cai: Number of the surviving insects at the time of the examination in untreated group;
- Tb: Number of the test insects in treated group;
- Tai: Number of the surviving insects at the time of the examination in treated group;

Here the "untreated group" represents a group where a similar treatment procedure to that of treated group except not using the test compound is done.

Test Example 7

The test was conducted according to the Test method 7 by making the prescribed concentration 500 ppm and using the below-mentioned present compounds as a test compound, and, as the result of the test, the below-mentioned present compounds showed 90% or more as the controlling value.
Present compound(s): 1, 2, 4, 6, 7, 8, 9, 10, 11, 12, 13, 14, 15, 16, 17, 19 and 20

Test Method 8

The test compounds are made to a formulation according to a similar method to that described in the Formulation Example 5, and thereto is added water to prepare a diluted solution containing a prescribed concentration of the test compound.

Thirty (30) last instar larvae of common house mosquito (*Culex pipiens pallens*) are released into the diluted solutions, and after 1 day, the number of the surviving insects is examined, and the mortality is determined. The mortality is calculated by the following equation.

$$\text{Mortality (\%)} = (\text{Number of dead insects})/\text{Number of tested insects} \times 100$$

Test Example 8

The test was conducted according to the Test method 8 by making the prescribed concentration 3.5 ppm and using the below-mentioned present compounds as a test compound, and, as the result of the test, the below-mentioned present compounds showed 91% or more as the mortality.
Present compound(s): 1, 2, 3, 4, 5, 6, 7, 8, 9, 10, 11, 12, 13, 14, 15, 17, 19 and 20

Test Method 9

The test compounds are made to a formulation according to a similar method to that described in the Formulation Example 5, and thereto is added water to prepare a diluted solution containing a prescribed concentration of the test compound. The prescribed concentration is any one of 500 ppm, 125 ppm, 31 ppm or 7.8 ppm.

The inner bottom of the cup having 5.5 cm diameter is matted with the same size of a filter paper, and 0.7 mL of the diluted solution is added dropwise to the filter paper, and 30 mg sucrose as bait is placed in the cup uniformly. Ten (10) female adult housefly (*Musca domestica*) are released into the cup, and the cup was covered with the lid. After 24 hours, the life and death of housefly is examined and the number of dead insects is counted and the mortality of insects is calculated. The mortality of insects is calculated by the following equation.

$$\text{Mortality (\%)} = (\text{Number of dead insects}/\text{Number of test insects}) \times 100$$

Test Example 9

The test was conducted according to the Test method 9 by making the prescribed concentration 500 ppm and using the below-mentioned present compounds as a test compound, and, as the result of the test, the below-mentioned present compounds showed 80% or more as the mortality.

Present compound(s): 1, 2, 4, 5, 6, 7, 8, 9, 10, 11, 12, 13, 14, 15, 16, 17, 19 and 20

Test Method 10

The test compounds are made to a formulation according to a similar method to that described in the Formulation Example 5, and thereto is added water to prepare a diluted solution containing a prescribed concentration of the test compound. The prescribed concentration is any one of 500 ppm, 125 ppm, 31 ppm or 7.8 ppm.

The inner bottom of the cup having 5.5 cm diameter is matted with the same size of a filter paper, and 0.7 mL of the diluted solution is added dropwise to the filter paper, and 30 mg sucrose as bait is placed in the cup uniformly. Two (2) male adult German cockroach (*Blattella germanica*) are released into the cup, and the cup was covered with the lid. After 6 days, the life and death of cockroach is examined and the number of dead insects is counted and the mortality of insects is calculated by the following equation.

Mortality (%)=(Number of dead insects/Number of test insects)×100

Test Example 10

The test was conducted according to the Test method 10 by making the prescribed concentration 500 ppm and using the below-mentioned present compounds as a test compound, and, as the result of the test, the below-mentioned present compounds showed 100% or more as the mortality. Present compound(s): 4, 6, 7, 8, 10, 12, 13, 14, 15, 17, 19 and 20

Test Method 11

An acetone solution which is adjusted to 200 ppm of the test compound is poured into a container having 20 mL contents, and the test compound is coated uniformly on inner face of the container and the container is then allowed to dry. The prescribed concentration is any one of 10 mg/m$^2$, 2.5 mg/m$^2$, 0.63 mg/m$^2$, 0.16 mg/m$^2$, 0.039 mg/m$^2$, or 0.0098 mg/m$^2$.

Five (5) female adult of common house mosquito (*Culex pipiens pallens*) are placed in the container, and the container is then covered with the lid. After 1 hour, the number of the dead insects is examined, and the mortality is calculated by the following equation.

Mortality (%)=(Number of dead insects/Number of tested insects)×100

Test Example 11

The test was conducted according to the Test method 11 by making the prescribed concentration 10 mg/m$^2$ and using the below-mentioned present compounds as a test compound, and, as the result of the test, the below-mentioned present compounds showed 80% or more as the mortality. Present compound(s): 1, 2, 4, 6, 7, 8, 9, 10, 14, 17 and 22

Test Method 12

An acetone solution which is adjusted to 200 ppm of the test compound is poured into a container having 20 mL contents, and the test compound is coated uniformly on inner face of the container and the container is then allowed to dry. The prescribed concentration is any one of 10 mg/m$^2$, 2.5 mg/m$^2$, 0.63 mg/m$^2$, 0.16 mg/m$^2$, 0.039 mg/m$^2$, or 0.0098 mg/m$^2$.

Five (5) female adult of common house mosquito (*Culex pipiens pallens*) are placed in the container, and the container is then covered with the lid. After 1 hour, the number of the dead insects is examined, and the mortality is calculated by the following equation.

Mortality (%)=(Number of dead insects/Number of tested insects)×100

Test Example 12

The test was conducted according to the Test method 12 by making the prescribed concentration 10 mg/m$^2$ and using the below-mentioned present compounds as a test compound, and, as the result of the test, the below-mentioned present compounds showed 80% or more as the mortality. Present compound(s): 1, 2, 4, 6, 7, 8, 9, 10, 14, 17 and 22

Test Method 13

A test compound is diluted with a mixed solution of isopropyl alcohol/kerosine=1/9 so as to prepare a solution containing a prescribed concentration of the test compound.

Ten (10) adult common house mosquitoes (*Culex pipens pallens*) are released in a plastic cup (bottom diameter 10.6 cm), and the cup is covered with a net. The cup is set at the inside bottom of a test chamber (bottom face: 46 cm×46 cm, height: 70 cm). Each 0.5 mL of the above-mentioned diluted solutions is sprayed using a spray gun (at a pressure of 0.4 kg/cm$^2$) from 30 cm higher than the upper face of the cup. Immediately after the spraying, the cup is pulled out from the test chamber. After 15 minutes, the number of knocked-down insects is counted, and a knock-down ratio is determined. The number of knocked-down insects is calculated by the following equation.

Knocked-down ratio (%)=(Number of knocked-down insects/Number of test insects)×100

Test Example 13

The test was conducted according to the Test method 13 by making the prescribed concentration 0.5% w/v and using the below-mentioned present compounds as a test compound, and, as the result of the test, the below-mentioned present compounds showed 80% or more as the mortality. Present compound(s): 1, 2, 3, 4, 5, 6, 7, 8, 10, 11, 12, 13, 14, 15, 16, 22, 23, and 24

INDUSTRIAL APPLICABILITY

The present compound shows an excellent control effect against a harmful arthropod.

The invention claimed is:
1. A compound represented by formula (I):

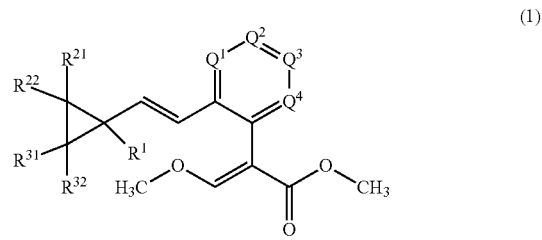

wherein
R$^1$ represents a C1-C3 alkyl group which may optionally have one or more halogen atoms or a hydrogen atom, $R^{21}$, $R^{22}$, $R^{31}$ and $R^{32}$ are identical to or different from each other and each represents a C1-C4 chain hydrocarbon group which may optionally have one or more halogen atoms, a halogen atom, or a hydrogen atom, $Q^1$ represents $CX^1$ or a nitrogen atom,
$Q^2$ represents $CX^2$ or a nitrogen atom,
$Q^3$ represents $CX^3$ or a nitrogen atom,
$Q^4$ represents $CX^4$ or a nitrogen atom, and
$X^1$, $X^2$, $X^3$ and $X^4$ are identical to or different from each other and each represents a C1-C4 chain hydrocarbon group wherein the C1-C4 chain hydrocarbon group may optionally have one or more substituents selected from the group consisting of a C1-C3 alkoxy group and a halogen atom, a C1-C4 alkoxy group which may optionally have one or more halogen atoms, a halogen atom, or a hydrogen atom.

2. The compound of claim 1 wherein $Q^1$, $Q^3$ and $Q^4$ are CH, and $Q^2$ represents $CX^2$.

3. The compound of claim 1 wherein $Q^2$ represents $CCH_3$.

4. The compound of claim 1 wherein $Q^2$ represents CH.

5. The compound of claim 1 wherein $R^1$ represents a hydrogen atom.

6. The compound of claim 1 wherein $R^{21}$, $R^{22}$, $R^{31}$ and $R^{32}$ represent a hydrogen atom.

7. A composition for controlling harmful arthropod comprising the compound of claim 1 and an inert carrier.

8. A method for controlling harmful arthropod which comprises applying an effective amount of the compound of claim 1 to a harmful arthropod or a habitat of the harmful arthropod.

\* \* \* \* \*